United States Patent
Lizée et al.

(10) Patent No.: US 11,684,657 B2
(45) Date of Patent: Jun. 27, 2023

(54) HLA-RESTRICTED VGLL1 PEPTIDES AND USE THEREOF IN PROMOTING AN IMMUNE RESPONSE IN A SUBJECT

(71) Applicant: Board of Regents, The University of Texas System, Austin, TX (US)

(72) Inventors: Gregory Lizée, Houston, TX (US); Cassian Yee, Houston, TX (US); Janos Roszik, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1032 days.

(21) Appl. No.: 16/339,981

(22) PCT Filed: Oct. 5, 2017

(86) PCT No.: PCT/US2017/055414
§ 371 (c)(1),
(2) Date: Apr. 5, 2019

(87) PCT Pub. No.: WO2018/067869
PCT Pub. Date: Apr. 12, 2018

(65) Prior Publication Data
US 2020/0040079 A1 Feb. 6, 2020

Related U.S. Application Data

(60) Provisional application No. 62/405,779, filed on Oct. 7, 2016.

(51) Int. Cl.
| | |
|---|---|
| *A61K 38/08* | (2019.01) |
| *A61K 38/17* | (2006.01) |
| *A61K 39/00* | (2006.01) |
| *A61P 35/00* | (2006.01) |
| *A61P 37/04* | (2006.01) |
| *C07K 14/47* | (2006.01) |
| *C07K 16/28* | (2006.01) |
| *C12N 5/0783* | (2010.01) |
| *C07K 7/06* | (2006.01) |
| *A61K 38/00* | (2006.01) |
| *A61K 45/06* | (2006.01) |

(52) U.S. Cl.
CPC .......... *A61K 39/0011* (2013.01); *A61K 38/08* (2013.01); *A61K 38/1709* (2013.01); *A61P 37/04* (2018.01); *C07K 14/4748* (2013.01); *C07K 16/2818* (2013.01); *C12N 5/0638* (2013.01); *A61K 38/00* (2013.01); *A61K 45/06* (2013.01); *C07K 7/06* (2013.01); *C12N 2501/60* (2013.01); *C12N 2502/1121* (2013.01)

(58) Field of Classification Search
CPC .... A61K 39/0011; A61K 38/08; A61K 39/00; A61K 38/1709; C07K 14/4748; C07K 7/06; C07K 14/47; A61P 35/00; A61P 37/04

See application file for complete search history.

(56) References Cited

U.S. PATENT DOCUMENTS

| | | |
|---|---|---|
| 7,910,109 B2 | 3/2011 | Carroll et al. |
| 8,586,006 B2 | 11/2013 | Hood et al. |
| 8,617,562 B2 | 12/2013 | Tsunoda et al. |
| 9,061,059 B2 | 6/2015 | Chakraborty et al. |
| 9,089,604 B2 | 7/2015 | Chakraborty et al. |
| 2014/0147432 A1 | 5/2014 | Bancel et al. |
| 2015/0224182 A1 | 8/2015 | Hunt et al. |

FOREIGN PATENT DOCUMENTS

| | | |
|---|---|---|
| KR | 10-2015-0050681 | 5/2015 |
| WO | WO 2003/003906 | 1/2003 |

OTHER PUBLICATIONS

"Supplementary Information" for Bradley et al, 2022. Nature Communications 11(1): 5332; PDF labeled "41467_2020_19141_MOESM1_ESM.pdf" available at https://www.ncbi.nlm.nih.gov/pmc/articles/PMC7577998/; PDF consists of 29 pages.*
Bellone et al., "Generation of CA125-specific cytotoxic T lymphocytes in human leukocyte antigen-A2.1-positive healthy donors and patients with advanced ovarian cancer," *Am J Obstet Gynecol*, 200:75.e1-75.e10, 2009.
Extended European Search Report issued in European Application No. 17859215.0, dated Jun. 9, 2020.
Jiao et al., "A Peptide Mimicking VGLL4 Function Acts as a YAP Antagonist Therapy against Gastric Cancer," *Cancer Cell*, 25:166-180, 2014.
MD Anderson Cancer Center, "Researchers aim to overcome multiple obstacles in pancreatic cancer," *DoCMessages*, 13(2):11-12, 2016.
PCT International Search Report and Written Opinion issued in International Application PCT/2017/055414, dated Jan. 9, 2018.
Xu et al., "An integrated genome-wide approach to discover tumor-specific antigens as potential immunologic and clinical targets in cancer," *Cancer Res.*, 72(24):6351-6361, 2012.
Yoshida et al., "Expression patterns of epiplakin1 in pancreas, pancreatic cancer and regenerating pancreas," *Genes to Cells*, 13(7):667-678, 2008.
Bradley et al., "Vestigial-like 1 is a shared targetable cancer-placenta antigen expressed by pancreatic and basal-like breast cancers," *Nature Communications*, 11(1):5332, 2020.
PCT International Search Report and Written Opinion issued in International Application No. PCT/US2021/033619, dated Dec. 23, 2021.

\* cited by examiner

*Primary Examiner* — Zachary C Howard
(74) *Attorney, Agent, or Firm* — Parker Highlander PLLC

(57) ABSTRACT

Provided herein are tumor-antigen VGLL1 specific peptides. Also provided herein are methods of generating VGLL1-specific T cells and their use for the treatment of cancer. In addition, the VGLL1-specific peptides may be used as a vaccine.

17 Claims, 18 Drawing Sheets

Specification includes a Sequence Listing.

NATURAL VGLL1 PEPTIDE:

LSELETPGKY

| #1 | Seq. | b+ |
|---|---|---|
| 1 | L | 114.09135 |
| 2 | S | 201.12338 |
| 3 | E | 330.16598 |
| 4 | L | 443.25005 |
| 5 | E | 572.29265 |
| 6 | T | 673.34033 |
| 7 | P | 770.39310 |
| 8 | G | 827.41457 |
| 9 | K | 955.50954 |
| 10 | Y | |

PREDICTED MASSES of 'b' ions:

All are identical *except for 'b9'*, which contains the heavy lysine (K)

ISOTOPE-LABELED PEPTIDE:

LSELETPGKY  ↑ Heavy lysine ($C^{15} + N^{13}$)

| b+ | Seq. | #1 |
|---|---|---|
| 114.09135 | L | 1 |
| 201.12338 | S | 2 |
| 330.16598 | E | 3 |
| 443.25005 | L | 4 |
| 572.29265 | E | 5 |
| 673.34033 | T | 6 |
| 770.39310 | P | 7 |
| 827.41457 | G | 8 |
| 963.52374 | K-Label13 | 9 |
| | Y | 10 |

| #2 | Seq. | y+ |
|---|---|---|
| 10 | L | |
| 9 | S | 1023.49935 |
| 8 | E | 936.46732 |
| 7 | L | 807.42472 |
| 6 | E | 694.34065 |
| 5 | T | 565.29805 |
| 4 | P | 464.25037 |
| 3 | G | 367.19760 |
| 2 | K | 310.17613 |
| 1 | Y | 182.09116 |

PREDICTED MASSES of 'y' ions:

All are shifted up by 8 units, *except for 'y1'*, which contains no heavy lysine (K)

| y+ | Seq. | #2 |
|---|---|---|
| | L | 10 |
| 1031.51395 | S | 9 |
| 944.48152 | E | 8 |
| 815.43892 | L | 7 |
| 702.35485 | E | 6 |
| 573.31225 | T | 5 |
| 472.26457 | P | 4 |
| 375.21180 | G | 3 |
| 318.19033 | K-Label13 | 2 |
| 182.09116 | Y | 1 |

'b' ions
$b_1$  $X_1$ — $X_2X_3X_4X_5X_6X_7X_8X_9$  $y_9$
$b_2$  $X_1X_2$ — $X_3X_4X_5X_6X_7X_8X_9$  $y_8$
$b_3$  $X_1X_2X_3$ — $X_4X_5X_6X_7X_8X_9$  $y_7$
$b_4$  $X_1X_2X_3X_4$ — $X_5X_6X_7X_8X_9$  $y_6$
$b_5$  $X_1X_2X_3X_4X_5$ — $X_6X_7X_8X_9$  $y_5$
$b_6$  $X_1X_2X_3X_4X_5X_6$ — $X_7X_8X_9$  $y_4$
$b_7$  $X_1X_2X_3X_4X_5X_6X_7$ — $X_8X_9$  $y_3$
$b_8$  $X_1X_2X_3X_4X_5X_6X_7X_8$ — $X_9$  $y_2$ 'y' ions

FIG. 1D

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Leu Ser Glu Leu Glu Thr Pro Gly Lys Tyr
1               5                   10
```

HLA-RESTRICTED VGLL1 PEPTIDES AND USE THEREOF IN PROMOTING AN IMMUNE RESPONSE IN A SUBJECT

This application is a national phase application under 35 U.S.C. § 371 of International Application No. PCT/US2017/055414, filed Oct. 5, 2017, which claims the benefit of U.S. Provisional Patent Application No. 62/405,779, filed Oct. 7, 2016, the entirety of each of which is incorporated herein by reference.

The sequence listing that is contained in the file named "UTFCP1307WO_ST25.txt", which is 1 KB (as measured in Microsoft Windows) and was created on Oct. 5, 2017, is filed herewith by electronic submission and is incorporated by reference herein.

BACKGROUND OF THE INVENTION

1. Field of the Invention

The present invention relates generally to the fields of immunology and medicine. More particularly, it concerns tumor antigen-specific peptides and uses thereof for the treatment of cancer.

2. Description of Related Art

Adoptive T cell therapy (ACT; also referred to as "adoptive cell transfer") has shown promise as a method for treating melanoma; unfortunately, this approach has also been hindered by limitations including toxicity towards non-cancerous tissues. ACT generally involves infusing a large number of autologous activated tumor-specific T cells into a patient, e.g., to treat a cancer. ACT has resulted in therapeutic clinical responses in melanoma patients (Yee 2002; Dudley 2002; Yee 2014). Generally, to develop effective anti-tumor T cell responses, the following three steps are normally required: priming and activating antigen-specific T cells, migrating activated T cells to the tumor site, and recognizing and killing the tumor by antigen-specific T cells. The choice of the target antigen is important for induction of effective antigen-specific T cells.

While several tumor-associated antigens have been identified for melanoma and a handful of other solid tumor malignancies, there is a paucity of immunogenic targets for pancreatic, ovarian, gastric, lung, cervical, breast, and head and neck cancer. Thus, identification and validation of novel epitopes and target antigens for these common and difficult to treat malignancies is warranted.

SUMMARY OF THE INVENTION

In some embodiments, the present disclosure provides VGLL1 peptides and methods for their use, such as in therapies including adoptive T cell therapies. In some embodiments, the peptides may be used to expand VGLL1-specific T cells in vitro that are administered to a mammalian subject, such as a human patient, to treat a disease (e.g., a cancer). In further embodiments, the T cells are genetically engineered to express T cell receptors (TCRs) with antigenic specificity for VGLL1. In other embodiments, the peptides may be administered to a mammalian subject to induce an immune response or vaccinate the subject against the peptide, and such an immune response may be useful to treat or reduce the chances of getting or relapsing from a disease, such as a cancer.

In one embodiment, the present disclosure provides an isolated VGLL1 peptide of 35 amino acids in length or less (e.g., 34, 33, 32, 31, or 30 amino acids) comprising an amino acid sequence having at least 90% sequence identity to SEQ ID NO:1 (LSELETPGKY), wherein the peptide is capable of inducing cytotoxic T lymphocytes (CTLs). In some aspects, the peptide comprises an amino acid sequence having at least 91, 92, 93, 94, 95, 96, 97, 98, 99, or 100 percent sequence identity to SEQ ID NO: 1. In certain aspects, the peptide is 30 amino acids in length or less, such as 29, 28, 27, 26, 25, 24, 23, 22, 21, 20, 19, 18, 17, 16, 15, 14, 13, 12, 11, or 10 amino acids in length.

In some aspects, the peptide binds to a human class I HLA protein. In particular aspects, the human class I HLA protein is HLA-A*0101 or other members of the HLA-A1 family, such as HLA-A*0102 and HLA-A*0103. In other aspects, the class I HLA protein is HLA-A*2902 or other members of the HLA-A29 family, or HLA-A*3002 and other members of the HLA-A30 family. In other aspects, the class I HLA protein is HLA-B*1801 or other members of the HLA-B18 family or HLA-B*4403 or other members of the HLA-B44 family.

In another embodiment, there is provided a pharmaceutical composition comprising the isolated VGLL1 peptide of the embodiments and a pharmaceutical carrier. In some aspects, the pharmaceutical composition is formulated for parenteral administration, intravenous injection, intramuscular injection, inhalation, or subcutaneous injection. In certain aspects, the peptide is comprised in a liposome, lipid-containing nanoparticle, or in a lipid-based carrier. In some aspects, the pharmaceutical preparation is formulated for injection or inhalation as a nasal spray.

A further embodiment provides an isolated nucleic acid encoding the VGLL1 peptide of the embodiments. Also provided herein is a vector comprising a contiguous sequence consisting of the nucleic acid encoding the VGLL1 peptide.

In yet another embodiment, there is provided a method of promoting an immune response in a subject, comprising administering an effective amount of the VGLL1 peptide of the embodiments to the subject, wherein the peptide induces antigen-specific T cells in the subject. In some aspects, the subject is diagnosed with cancer. In certain aspects, the cancer is pancreatic, ovarian, gastric, or breast cancer. In particular aspects, the subject is a human.

In additional aspects, the method further comprises administering at least a second anti-cancer therapy. In some aspects, the second anti-cancer therapy is selected from the group consisting of a chemotherapy, a radiotherapy, an immunotherapy, or a surgery. In particular aspects, the immunotherapy is an immune checkpoint inhibitor. In one specific aspects, the immune checkpoint inhibitor is an anti-PD1 monoclonal antibody.

A further embodiment provides a method of producing VGLL1-specific T cells comprising obtaining a starting population of T cells, and contacting the starting population of T cells with the VGLL1 peptide (e.g., a peptide of SEQ ID NO: 1) of the embodiments, thereby generating VGLL1-specific T cells. In some aspects, contacting is further defined as co-culturing the starting population of T cells with antigen presenting cells (APCs), wherein the APCs present the VGLL1 peptide of the embodiments on their surface. In particular aspects, the APCs are dendritic cells. In some aspects, the starting population of T cells are CD8$^+$ T cells. In certain aspects, the T cells are CTLs. In some aspects, obtaining comprises isolating the starting population of T cells from peripheral blood mononuclear cells (PBMCs).

Also provided herein is a pharmaceutical composition comprising the VGLL1-specific T cells produced by the methods herein.

An even further embodiment provides an antigen receptor, such as a T cell receptor (TCR) or chimeric antigen receptor (CAR), with antigenic specificity for VGLL1. Another embodiment provides T cells engineered to express a VGLL1-specific TCR or CAR. In some aspects, the VGLL1-specific chimeric antigen receptor comprises an intracellular signaling domain, a transmembrane domain, and/or an extracellular domain. In certain aspects, DNA encoding the CAR is integrated into the genome of the cell. In some aspects, the extracellular domain of the CAR comprises a VGLL1-binding region. For example, the VGLL1-binding region may be a F(ab')2, Fab', Fab, Fv, or scFv. In certain aspects, the intracellular signaling domain of the CAR is a T-lymphocyte activation domain. For example, the intracellular signaling domain of the CAR may comprise CD3ξ, CD28, OX40/CD134, 4-1BB/CD137, FcεRIγ, ICOS/CD278, ILRB/CD122, IL-2RG/CD132, DAP molecules, CD70, cytokine receptor, CD40, or a combination thereof. In certain aspects, the transmembrane domain of the CAR comprises CD28 transmembrane domain, IgG4Fc hinge, Fc regions, CD4 transmembrane domain, the CD3ξ transmembrane domain, cysteine mutated human CD3ξ domain, CD16 transmembrane domain, CD8 transmembrane domain, or erythropoietin receptor transmembrane domain.

Another embodiment provides a method of treating cancer in a subject comprising administering an effective amount of the VGLL1-specific T cells of the embodiments to the subject. In some aspects, the cancer is pancreatic, ovarian, gastric, bladder, or breast cancer. In particular aspects, the subject is a human. In some aspects, the antigen-specific T cells are autologous. In some aspects, the subject is determined to have cancer cells which express VGLL1.

In certain aspects, the method further comprises lymphodepletion of the subject prior to administration of the antigen-specific T cells. In some aspects, lymphodepletion comprises administration of cyclophosphamide and/or fludarabine.

In some aspects, the method further comprises administering at least a second therapeutic agent. In certain aspects, the at least a second therapeutic agent comprises chemotherapy, immunotherapy, surgery, radiotherapy, or biotherapy. In particular aspects, the immunotherapy is an immune checkpoint inhibitor. In one specific aspects, the immune checkpoint inhibitor is an anti-PD1 monoclonal antibody.

In certain aspects, the VGLL1-specific T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

Further provided herein is a composition comprising an effective amount of the VGLL1-specific T cells of the embodiments for the treatment of cancer in a subject. In some aspects, the cancer is pancreatic, ovarian, gastric, bladder, or breast cancer. In particular aspects, the subject is a human. In some aspects, the antigen-specific T cells are autologous. In some aspects, the subject is determined to have cancer cells which express VGLL1.

Further provided herein are methods of determining the prognosis of a subject with cancer comprising measuring the expression level of VGLL1 in a sample obtained from said subject, wherein an elevated level of VGLL1 identifies a subject with a poor prognosis. In some aspects, the sample is a blood sample or tissue sample, such as a tumor sample. In particular aspects, the cancer is pancreatic cancer.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-1D: Mass spectrometry-based identification of a pancreatic tumor-associated antigen derived from VGLL1. (A) Tandem mass spectrometry (MS) analysis of an HLA class I-bound VGLL1 peptide, LSELETPGKY (SEQ ID NO:1), isolated from a pancreatic tumor organoid cell line (hMIA-2D) derived from PDAC patient MP015. The top panel shows the spectra of the original eluted peptide from discovery phase tandem MS. The middle and bottom spectra show a targeted MS experiment in which the isotope-labeled synthetic peptide LSELETPGKY (SEQ ID NO:1) (with heavy lysine residue underlined) was spiked into the tumor sample and co-eluted with the native peptide, demonstrating gold standard confirmation of peptide identity. (B) Same mass spectra as in (A), but with 'y' ions circled to highlight the expected mass shift of 8 atomic mass units for the isotope-labeled peptide, corresponding to the heavy lysine residue. (C) Same mass spectra as in (A), but with 'b' ions circled to highlight the expected mass shift of 8 atomic mass units for only the $b_{9+}$ ion, but no other 'b' ions. (D) Analysis of expected tandem MS fragment ion masses for the native and isotope-labeled VGLL1 peptide LSELETPGKY (SEQ ID NO: 1) and LSELETPG$\underline{K}$Y (SEQ ID NO: 1).

DESCRIPTION OF ILLUSTRATIVE EMBODIMENTS

Figure 1A:
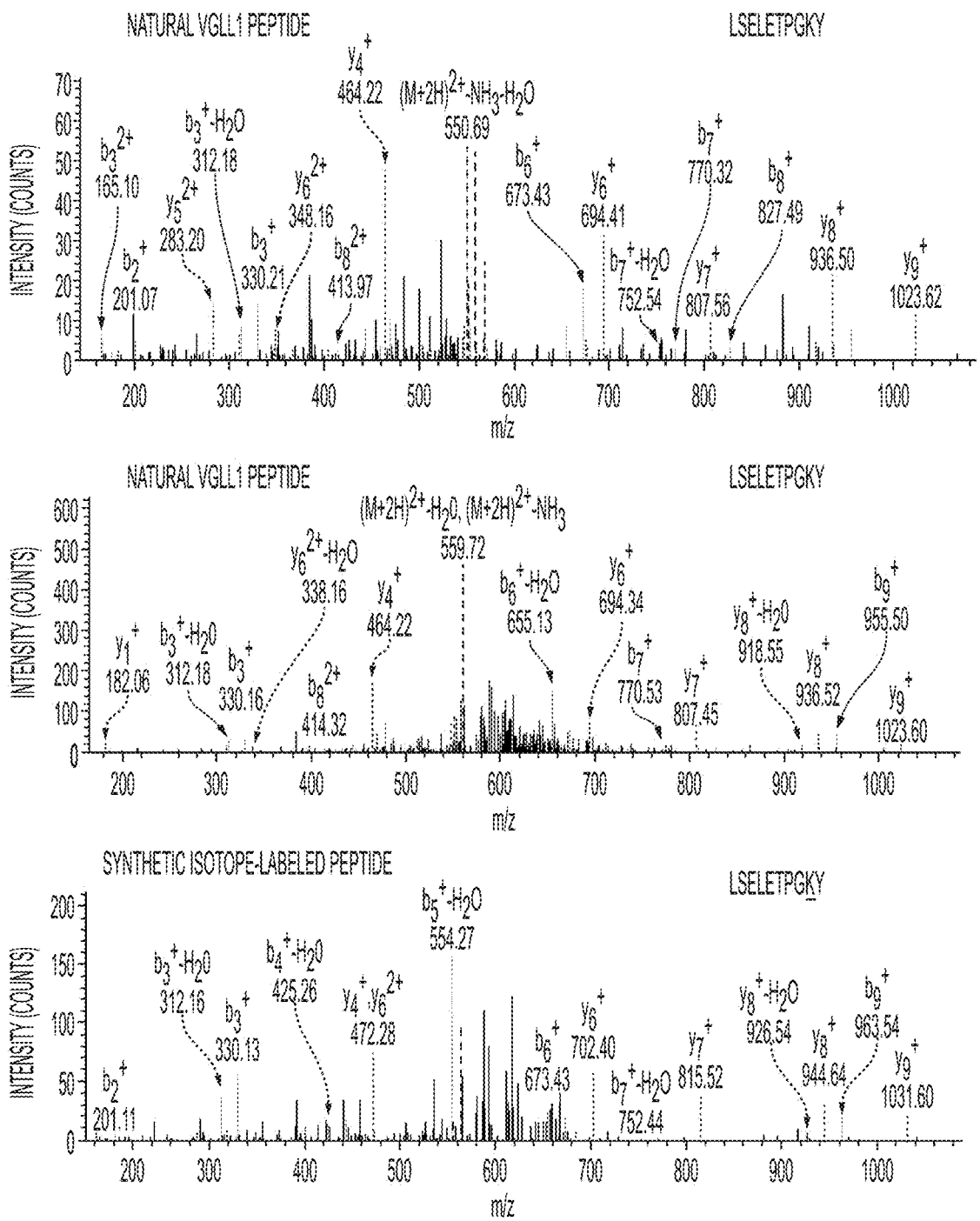
Figure 1B:
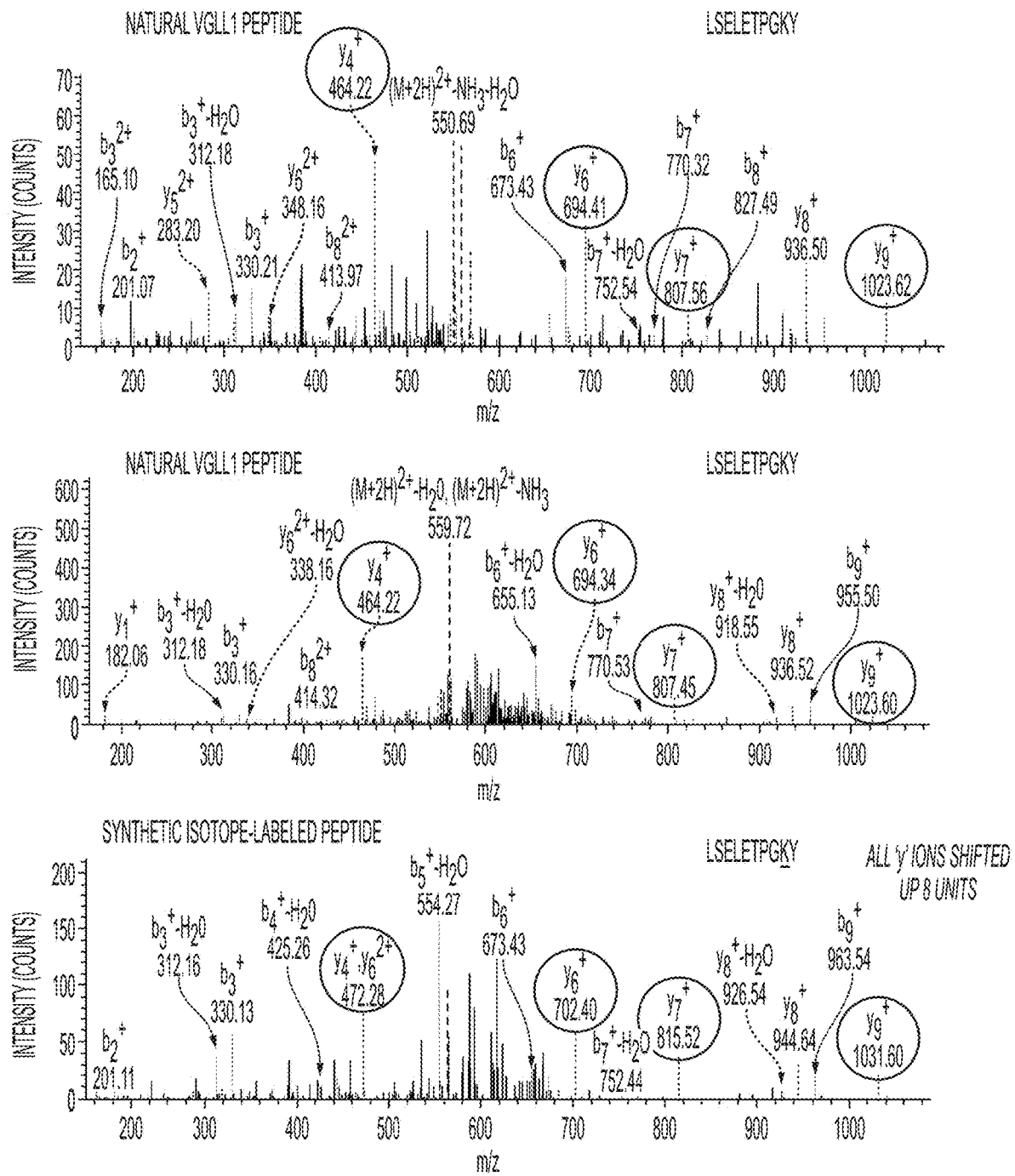
Figure 1C:
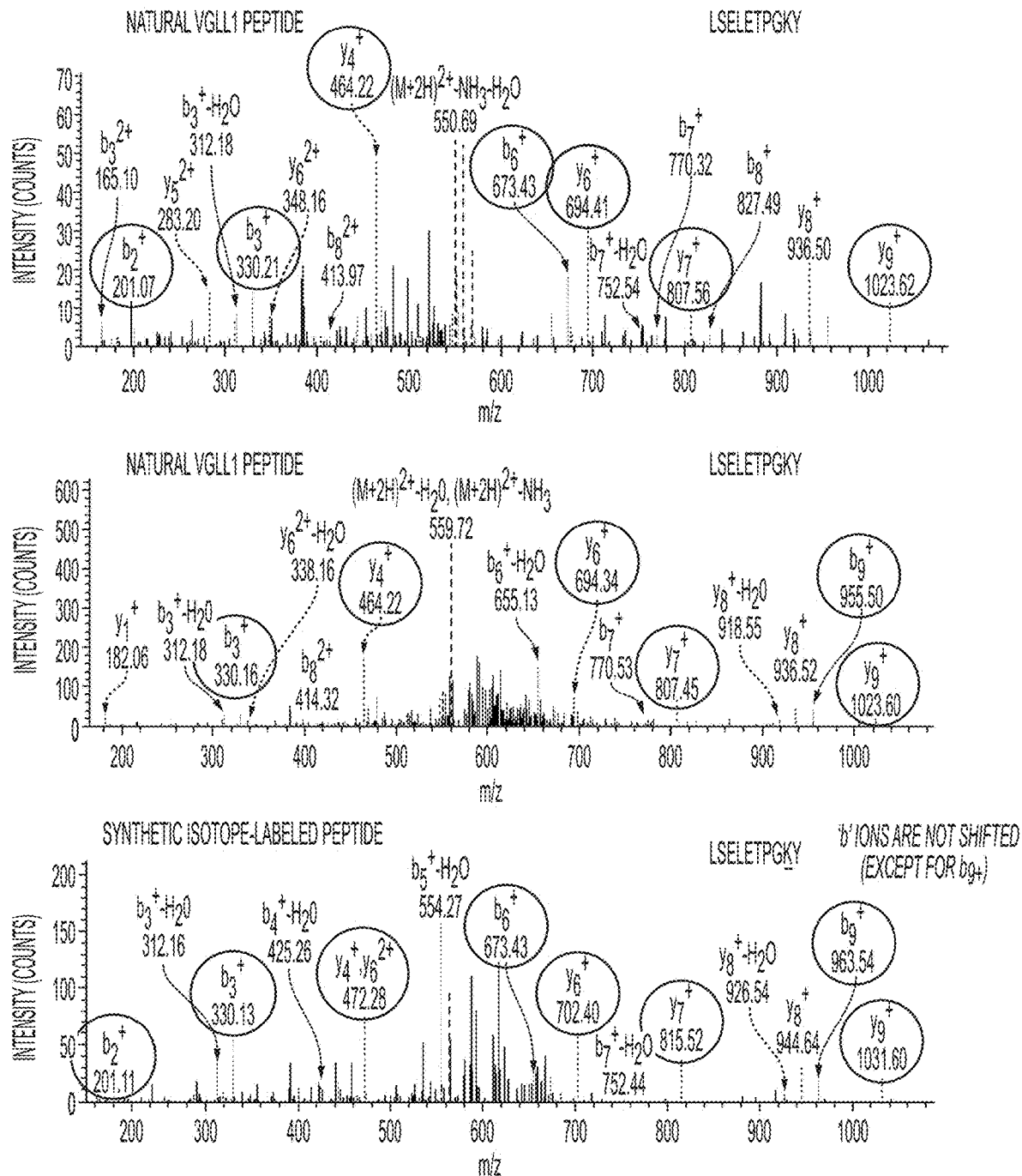

For patients with many different cancer types, T cell based immunotherapies represent a promising approach with proven efficacy. However, antigen-specific T cell therapy for most cancer types is not feasible due to the lack of tumor-associated antigens currently known, which has stalled their clinical development. Studies in the present disclosure profiled the immunopeptidome of pancreatic cell lines and tumor specimens through mass spectrophotometry and identified peptide epitopes derived from a novel tumor-associated antigen VGLL1 that is expressed at substantially higher levels in pancreatic, ovarian, gastric, bladder, and breast cancer compared with normal tissues. Using these peptide epitopes, antigen-specific cytotoxic T lymphocytes (CTLs) were generated from pancreatic patient peripheral blood mononuclear cells (PBMCs) that recognized the endogenously-presented antigen on HLA-matched allogeneic tumor cell lines, leading to tumor cell killing. Thus, these antigen-specific CTLs provided herein may be used to target solid cancers (e.g., pancreatic, ovarian, gastric, and breast cancer).

Accordingly, the present disclosure provides tumor antigen-specific peptides, such as to tumor antigen VGLL1, for use as immunotherapy for the treatment of a cancer. The present studies identified VGLL1 as a tumor-associated antigen from a pancreatic elution. The VGLL1 peptide had a predicted HLA-A*0101 affinity of 51 nM which has a world prevalence of 10-20%. Thus, in some embodiments, VGLL1 peptides (e.g. comprising SEQ ID NO:1) are provided herein. For example, a VGLL1-specific peptide may be contacted with or used to stimulate a population of T cells to induce proliferation of the T cells that recognize or bind the VGLL1-specific peptide. In other embodiments, a VGLL1-specific peptide of the present disclosure may be administered to a subject, such as a human patient, to enhance the immune response of the subject against a cancer.

A VGLL1-specific peptide may be included in an active immunotherapy (e.g., a cancer vaccine) or a passive immunotherapy (e.g., an adoptive immunotherapy). Active immunotherapies include immunizing a subject with a purified tumor antigen or an immunodominant VGLL1-specific peptide (native or modified). Alternately, antigen presenting cells (APCs) pulsed with a VGLL1-specific peptide (or transfected with genes encoding the tumor antigen) may be administered to a subject. The VGLL1-specific peptide may be modified or contain one or more mutations, such as a substitution mutation. Passive immunotherapies include adoptive immunotherapies. Adoptive immunotherapies generally involve administering cells to a subject, wherein the cells (e.g., CTLs) have been sensitized in vitro to the VGLL1-specific peptide (see, e.g., U.S. Pat. No. 7,910,109), such as by using APCs to present the VGLL1 epitope to the CTLs in vitro.

It was observed in the present studies that survival rate corresponds with VGLL1 expression as the lowest VGLL1 expression correlated with the highest survival rate. Thus, VGLL1 is a tumor marker that may be used as a prognostic marker in cancer patients, specifically pancreatic cancer patients.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a T cell therapy.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations. e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multi-specific antibody, etc., and that an antibody comprising the altered target binding sequence is also a monoclonal antibody. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride. Ringer's dextrose. etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject. In some embodiments, the dosage of antigen-specific T cell infusion may comprise about 100 million to about 30 billion cells, such as 10, 15, or 20 billion cells.

The term "immune checkpoint" refers to a molecule such as a protein in the immune system which provides inhibitory signals to its components in order to balance immune reactions. Known immune checkpoint proteins comprise CTLA-4, PD-1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

As used herein, a "protective immune response" refers to a response by the immune system of a mammalian host to a cancer. A protective immune response may provide a therapeutic effect for the treatment of a cancer, e.g., decreasing tumor size or increasing survival.

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18. Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtcin+SPupdate+PIR.

II. VGLL1 Peptides

Certain embodiments of the present disclosure concern tumor antigen-specific peptides, such as to the VGLL1 tumor antigen. In particular embodiments, the tumor antigen-specific peptides have the amino acid sequence of a VGLL1 peptide (LSELETPGKY: SEQ ID NO:1). The tumor antigen-specific peptide may have an amino acid sequence with at least 80, 85, 90, 95, 96, 97, 98, 99, or 100 percent sequence identity with the peptide sequences of SEQ ID NO:1.

As used herein, the term "peptide" encompasses amino acid chains comprising 7-35 amino acids, preferably 8-35 amino acid residues, and even more preferably 8-25 amino acids, or 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acids in length, or any range derivable therein. For example, a VGLL1 peptide of the present disclosure may, in some embodiments, comprise or consist of the VGLL1 peptide of SEQ ID NO:1. As used herein, an "antigenic peptide" is a peptide which, when introduced into a vertebrate, can stimulate the production of antibodies in the vertebrate, i.e., is antigenic, and wherein the antibody can selectively recognize and/or bind the antigenic peptide. An antigenic peptide may comprise an immunoreactive VGLL1 peptide, and may comprise additional sequences. The additional sequences may be derived from a native antigen and may be heterologous, and such sequences may, but need not, be immunogenic. In some embodiments, a tumor antigen-specific peptide (e.g., a VGLL1 peptide) can selectively bind with a HLA-A*0101. In certain embodiments, the VGLL1 peptide is 8, 9, 10, 11, 12, 13, 14, 15, 16, 17, 18, 19, 20, 21, 22, 23, 24, 25, 26, 27, 28, 29, 30, 31, 32, 33, 34, or 35 amino acids in length, or any range derivable therein. Preferably, the tumor antigen-specific peptide (e.g., a VGLL1 peptide) is from 8 to 35 amino acids in length. In some embodiments, the tumor antigen-specific peptide (e.g., a VGLL1 peptide) is from 8 to 10 amino acids in length.

As would be appreciated by one of skill in the art, MHC molecules can bind peptides of varying sizes, but typically not full length proteins. While MHC class I molecules have been traditionally described to bind to peptides of 8-11 amino acids long, it has been shown that peptides 15 amino acids in length can bind to MHC class I molecules by bulging in the middle of the binding site or extending out of the MHC class I binding groove (Guo et al., 1992; Burrows et at, 2006; Samino et al., 2006; Stryhn et al., 2000; Collins et al., 1994; Blanchard and Shastri, 2008). Further, recent studies also demonstrated that longer peptides may be more efficiently endocytosed, processed, and presented by antigen-presenting cells (Zwaveling et al., 2002; Bijker et al., 2007; Melief and van der Burg, 2008; Quintarelli et al., 2011). As demonstrated in Zwaveling et al. (2002) peptides up to 35 amino acids in length may be used to selectively bind a class II MHC and are effective. As would be immediately appreciated by one of skill, a naturally occurring full-length tumor antigen, such as VGLL1, would not be useful to selectively bind a class II MHC such that it would be endocytosed and generate proliferation of T cells. Generally, the naturally occurring full-length tumor antigen proteins do not display these properties and would thus not be useful for these immunotherapy purposes.

In certain embodiments, a tumor antigen-specific peptide (e.g., a VGLL1 peptide) is immunogenic or antigenic. As shown in the below examples, tumor antigen-specific peptides (e.g., a VGLL1 peptide) of the present disclosure can promote the proliferation of T cells. It is anticipated that such peptides may be used to induce some degree of protective immunity.

A tumor antigen-specific peptide (e.g., a VGLL1 peptide) may be a recombinant peptide, synthetic peptide, purified peptide, immobilized peptide, detectably labeled peptide, encapsulated peptide, or a vector-expressed peptide (e.g., a peptide encoded by a nucleic acid in a vector comprising a heterologous promoter operably linked to the nucleic acid). In some embodiments, a synthetic tumor antigen-specific peptide (e.g., a VGLL1 peptide) may be administered to a subject, such as a human patient, to induce an immune response in the subject. Synthetic peptides may display certain advantages, such as a decreased risk of bacterial contamination, as compared to recombinantly expressed peptides. A tumor antigen-specific peptide (e.g., a VGLL1 peptide) may also be comprised in a pharmaceutical composition such as, e.g., a vaccine composition, which is formulated for administration to a mammalian or human subject.

A. Cell Penetrating Peptides

In some embodiments, an immunotherapy may utilize a tumor antigen-specific peptide (e.g., a VGLL1 peptide) of the present disclosure that is associated with a cell penetrator, such as a liposome or a cell penetrating peptide (CPP). Antigen presenting cells (such as dendritic cells) pulsed with peptides may be used to enhance antitumour immunity (Celluzzi et al., 1996; Young et al., 1996). Liposomes and CPPs are described in further detail below. In some embodiments, an immunotherapy may utilize a nucleic acid encoding a tumor antigen-specific peptide (e.g., a VGLL1 peptide) of the present disclosure, wherein the nucleic acid is delivered, e.g., in a viral vector or non-viral vector.

A tumor antigen-specific peptide (e.g., a VGLL1 peptide) may also be associated with or covalently bound to a cell penetrating peptide (CPP). Cell penetrating peptides that may be covalently bound to a tumor antigen-specific peptide (e.g., a VGLL1 peptide) include, e.g., HIV Tat, herpes virus VP22, the *Drosophila* Antennapedia homeobox gene product, signal sequences, fusion sequences, or protegrin I. Covalently binding a peptide to a CPP can prolong the presentation of a peptide by dendritic cells, thus enhancing antitumour immunity (Wang and Wang, 2002). In some embodiments, a tumor antigen-specific peptide (e.g., the VGLL1 peptide) of the present disclosure (e.g., comprised within a peptide or polyepitope string) may be covalently bound (e.g., via a peptide bond) to a CPP to generate a fusion protein. In other embodiments, a tumor antigen-specific peptide (e.g., a VGLL1 peptide) or nucleic acid encoding a tumor antigen-specific peptide may be encapsulated within or associated with a liposome, such as a mulitlamellar, vesicular, or multivesicular liposome.

As used herein, "association" means a physical association, a chemical association or both. For example, an association can involve a covalent bond, a hydrophobic interaction, encapsulation, surface adsorption, or the like.

As used herein, "cell penetrator" refers to a composition or compound which enhances the intracellular delivery of the peptide/polyepitope string to the antigen presenting cell. For example, the cell penetrator may be a lipid which, when associated with the peptide, enhances its capacity to cross the plasma membrane. Alternatively, the cell penetrator may be a peptide. Cell penetrating peptides (CPPs) are known in the art, and include, e.g., the Tat protein of HIV (Frankel and Pabo, 1988), the VP22 protein of HSV (Elliott and O'Hare, 1997) and fibroblast growth factor (Lin et al., 1995).

Cell-penetrating peptides (or "protein transduction domains") have been identified from the third helix of the *Drosophila* Antennapedia homeobox gene (Antp), the HIV Tat, and the herpes virus VP22, all of which contain positively charged domains enriched for arginine and lysine residues (Schwarze et al., 2000; Schwarze et al., 1999). Also, hydrophobic peptides derived from signal sequences have been identified as cell-penetrating peptides. (Rojas et al., 1996; Rojas et al., 1998; Du et al., 1998). Coupling these peptides to marker proteins such as β-galactosidase has been shown to confer efficient internalization of the marker protein into cells, and chimeric, in-frame fusion proteins containing these peptides have been used to deliver proteins to a wide spectrum of cell types both in vitro and in vivo (Drin et al., 2002). Fusion of these cell penetrating peptides to a tumor antigen-specific peptide (e.g., a VGLL1 peptide) in accordance with the present disclosure may enhance cellular uptake of the polypeptides.

In some embodiments, cellular uptake is facilitated by the attachment of a lipid, such as stearate or myristilate, to the polypeptide. Lipidation has been shown to enhance the passage of peptides into cells. The attachment of a lipid moiety is another way that the present disclosure increases polypeptide uptake by the cell. Cellular uptake is further discussed below.

A tumor antigen-specific peptide (e.g., a VGLL1 peptide) of the present disclosure may be included in a liposomal vaccine composition. For example, the liposomal composition may be or comprise a proteoliposomal composition. Methods for producing proteoliposomal compositions that may be used with the present disclosure are described, e.g., in Neelapu et al. (2007) and Popescu et al. (2007). In some embodiments, proteoliposomal compositions may be used to treat a melanoma.

By enhancing the uptake of a tumor antigen-specific polypeptide, it may be possible to reduce the amount of protein or peptide required for treatment. This in turn can significantly reduce the cost of treatment and increase the supply of therapeutic agent. Lower dosages can also minimize the potential immunogenicity of peptides and limit toxic side effects.

In some embodiments, a tumor antigen-specific peptide (e.g., a VGLL1 peptide) may be associated with a nanoparticle to form nanoparticle-polypeptide complex. In some embodiments, the nanoparticle is a liposomes or other lipid-based nanoparticle such as a lipid-based vesicle (e.g., a DOTAP:cholesterol vesicle). In other embodiments, the nanoparticle is an iron-oxide based superparamagnetic nanoparticles. Superparamagnetic nanoparticles ranging in diameter from about 10 to 100 nm are small enough to avoid sequestering by the spleen, but large enough to avoid clearance by the liver. Particles this size can penetrate very small capillaries and can be effectively distributed in body tissues. Superparamagnetic nanoparticles-polypeptide complexes can be used as MRI contrast agents to identify and follow those cells that take up the tumor antigen-specific peptide (e.g., a VGLL1 peptide). In some embodiments, the nanoparticle is a semiconductor nanocrystal or a semiconductor quantum dot, both of which can be used in optical imaging. In further embodiments, the nanoparticle can be a nanoshell, which comprises a gold layer over a core of silica. One advantage of nanoshells is that polypeptides can be conjugated to the gold layer using standard chemistry. In other embodiments, the nanoparticle can be a fullerene or a nanotube (Gupta et al., 2005).

Peptides are rapidly removed from the circulation by the kidney and are sensitive to degradation by proteases in serum. By associating a tumor antigen-specific peptide (e.g., a VGLL1 peptide) with a nanoparticle, the nanoparticle-polypeptide complexes of the present disclosure may protect against degradation and/or reduce clearance by the kidney. This may increase the serum half-life of polypeptides, thereby reducing the polypeptide dose need for effective therapy. Further, this may decrease the costs of treatment, and minimizes immunological problems and toxic reactions of therapy.

B. Polyepitope Strings

In some embodiments, a tumor antigen-specific peptide (e.g., a VGLL1 peptide) is included or comprised in a polyepitope string. A polyepitope string is a peptide or polypeptide containing a plurality of antigenic epitopes from one or more antigens linked together. A polyepitope string may be used to induce an immune response in a subject, such as a human subject. Polyepitope strings have been previously used to target malaria and other pathogens (Baraldo et al., 2005; Moorthy et al., 2004; Baird et al., 2004). A polyepitope string may refer to a nucleic acid (e.g., a nucleic acid encoding a plurality of antigens including a VGLL1 peptide) or a peptide or polypeptide (e.g., containing a plurality of antigens including a VGLL1 peptide). A polyepitope string may be included in a cancer vaccine composition.

C. Biological Functional Equivalents

A tumor antigen-specific peptide (e.g., a VGLL1 peptide) of the present disclosure may be modified to contain amino acid substitutions, insertions and/or deletions that do not alter their respective interactions with an HLA class protein, such as HLA-A*0101, binding regions. Such a biologically functional equivalent of a tumor antigen-specific peptide (e.g., a VGLL1 peptide) could be a molecule having like or otherwise desirable characteristics, e.g., binding of HLA-A*0101. As a nonlimiting example, certain amino acids may be substituted for other amino acids in a tumor antigen-specific peptide (e.g., a VGLL1 peptide) disclosed herein without appreciable loss of interactive capacity, as demonstrated by detectably unchanged peptide binding to HLA-A*0101. In some embodiments, the tumor antigen-specific peptide has a substitution mutation at an anchor reside, such as a substitution mutation at one, two, or all of positions: 1 (P1), 2 (P2), and/or 9 (P9). It is thus contemplated that a tumor antigen-specific peptide (e.g., a VGLL1 peptide) disclosed herein (or a nucleic acid encoding such a peptide) which is modified in sequence and/or structure, but which is unchanged in biological utility or activity remains within the scope of the compositions and methods disclosed herein.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent peptides are thus defined herein as those peptides in which certain, not most or all, of the amino acids may be substituted. Of course, a plurality of distinct peptides with different substitutions may easily be made and used in accordance with the present disclosure.

The skilled artisan is also aware that where certain residues are shown to be particularly important to the biological or structural properties of a peptide, e.g., residues in specific epitopes, such residues may not generally be exchanged. This may be the case in the present disclosure, as a mutation in an tumor antigen-specific peptide (e.g., the VGLL1 peptide) disclosed herein could result in a loss of species-specificity and in turn, reduce the utility of the resulting peptide for use in methods of the present disclosure. Thus, peptides which are antigenic (e.g., bind HLA-A*0101 specifically) and comprise conservative amino acid substitutions are understood to be included in the present disclosure. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying a tumor antigen-specific peptide (e.g., a VGLL1 peptide) disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. In some embodiments, the mutation may enhance TCR-pMHC interaction and/or peptide-MHC binding.

The present disclosure also contemplates isoforms of the tumor antigen-specific peptides (e.g., a VGLL1 peptide) disclosed herein. An isoform contains the same number and kinds of amino acids as a peptide of the present disclosure, but the isoform has a different molecular structure. The isoforms contemplated by the present disclosure are those having the same properties as a peptide of the present disclosure as described herein.

Nonstandard amino acids may be incorporated into proteins by chemical modification of existing amino acids or by de novo synthesis of a peptide disclosed herein. A nonstandard amino acid refers to an amino acid that differs in chemical structure from the twenty standard amino acids encoded by the genetic code.

In select embodiments, the present disclosure contemplates a chemical derivative of a tumor antigen-specific peptide (e.g., a VGLL1 peptide) disclosed herein. "Chemical derivative" refers to a peptide having one or more residues chemically derivatized by reaction of a functional side group, and retaining biological activity and utility. Such derivatized peptides include, for example, those in which free amino groups have been derivatized to form specific salts or derivatized by alkylation and/or acylation, p-toluene sulfonyl groups, carbobenzoxy groups, t-butyloxycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein.

Preferred tumor antigen-specific peptides (e.g., a VGLL1 peptide) or analogs thereof preferably specifically or preferentially bind a HLA-A*0101. Determining whether or to what degree a particular tumor antigen-specific peptide or labeled peptide, or an analog thereof, can bind an HLA-A*0101 and can be assessed using an in vitro assay such as, for example, an enzyme-linked immunosorbant assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

D. Nucleic Acids Encoding a Tumor Antigen-Specific Peptide

In some aspects, the present disclosure provides a nucleic acid encoding an isolated antigen-specific peptide comprising a sequence that has at least about 90%, 91%, 92%, 93%, 94%, 95%, 96%, 97%, 98%, 99%, or 100% sequence identity SEQ ID NO:1, or the peptide may have 1, 2, 3, or 4 point mutations (e.g., substitution mutations) as compared to SEQ ID NO: 1. As stated above, such a tumor antigen-specific peptide may be, e.g., from 8 to 35 amino acids in length, or any range derivable therein. In some embodiments, the tumor antigen-specific peptide corresponds to a portion of the tumor antigen protein (e.g., VGLL1: NP_057351.1). The term "nucleic acid" is intended to include DNA and RNA and can be either double stranded or single stranded.

Some embodiments of the present disclosure provide recombinantly-produced tumor antigen-specific peptides (e.g., a VGLL1 peptide) which can specifically bind a HLA-A*0101. Accordingly, a nucleic acid encoding a tumor antigen-specific peptide may be operably linked to an expression vector and the peptide produced in the appropriate expression system using methods well known in the molecular biological arts. A nucleic acid encoding a tumor antigen-specific peptide disclosed herein may be incorporated into any expression vector which ensures good expression of the peptide. Possible expression vectors include but are not limited to cosmids, plasmids, or modified viruses (e.g. replication defective retroviruses, adenoviruses and adeno-associated viruses), so long as the vector is suitable for transformation of a host cell.

A recombinant expression vector being "suitable for transformation of a host cell" means that the expression vector contains a nucleic acid molecule of the present disclosure and regulatory sequences selected on the basis of the host cells to be used for expression, which is operatively linked to the nucleic acid molecule. The terms, "operatively linked" or "operably linked" are used interchangeably, and are intended to mean that the nucleic acid is linked to regulatory sequences in a manner which allows expression of the nucleic acid.

Accordingly, the present disclosure provides a recombinant expression vector comprising nucleic acid encoding a tumor antigen-specific peptide, and the necessary regulatory sequences for the transcription and translation of the inserted protein-sequence. Suitable regulatory sequences may be derived from a variety of sources, including bacterial, fungal, or viral genes (e.g., see the regulatory sequences described in Goeddel (1990).

Selection of appropriate regulatory sequences is generally dependent on the host cell chosen, and may be readily accomplished by one of ordinary skill in the art Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

A recombinant expression vector may also contain a selectable marker gene which facilitates the selection of host cells transformed or transfected with a recombinant tumor antigen-specific peptides (e.g., a VGLL1 peptide) disclosed herein. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as 3-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of a recombinant expression vector, and in particular, to determine the effect of a mutation on expression and phenotype. It will be appreciated that selectable markers can be introduced on a separate vector from the nucleic acid of interest.

Recombinant expression vectors can be introduced into host cells to produce a transformant host cell. The term "transformant host cell" is intended to include prokaryotic and eukaryotic cells which have been transformed or transfected with a recombinant expression vector of the present disclosure. The terms "transformed with", "transfected with", "transformation" and "transfection" are intended to encompass introduction of nucleic acid (e.g. a vector) into a cell by one of many possible techniques known in the art. Suitable host cells include a wide variety of prokaryotic and eukaryotic host cells. For example, the proteins of the present disclosure may be expressed in bacterial cells such as E. coli, insect cells (using baculovirus), yeast cells or mammalian cells.

A nucleic acid molecule of the present disclosure may also be chemically synthesized using standard techniques. Various methods of chemically synthesizing polydeoxynucleotides are known, including solid-phase synthesis which, like peptide synthesis, has been fully automated in commercially available DNA synthesizers (see e.g., U.S. Pat. Nos. 4,598,049; 4,458,066; 4,401,796; and 4,373,071).

III. Adoptive T Cell Therapy

Certain embodiments of the present disclosure concern obtaining and administering T cells to a subject as an immunotherapy to target cancer cells. In particular, the T cells are antigen-specific T cells (e.g., VGLL1-specific T cells). Several basic approaches for the derivation, activation and expansion of functional anti-tumor effector T cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

A. T Cell Preparation

In some embodiments, the T cells are derived from the blood, bone marrow, lymph, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) *Blood*. 1:72-82; Wang et al. (2012) *J Immunother.* 35(9):689-701.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A1 (HLA-A1) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A1-expressing antigen-presenting cells. Alternatively, the T-cells can be re-stimulated with irradiated, autologous lymphocytes or with irradiated HLA-A1+ allogeneic lymphocytes and IL-2, for example.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. Genetically Engineered Antigen Receptors

The T cell can genetically engineered to express antigen receptors such as engineered TCRs and/or CARs. For example, the autologous T-cells are modified to express a TCR having antigenic specificity for a cancer antigen. In particular embodiments, the antigen receptors have antigenic specificity for VGLL1. Suitable methods of modification are known in the art. See, for instance, Sambrook and Ausubel. For example, the T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009).

In some embodiments, the T cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687. WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., *Cancer Discov.* 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 March 18(2): 160-75. In some aspects, the genetically engineered antigen receptors include a CAR as described in U.S. Pat. No. 7,446,190, and those described in International Patent Application Publication No.: WO/2014055668 A1.

1. Chimeric Antigen Receptors

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e., comprise at least the transmembrane region(s) of) the alpha, beta or zeta chain of the T-cell receptor, CD28, CD3 epsilon, CD45, CD4, CD5, CDS, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3' chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain. CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta, CD3-Q or Fc receptor γ and CD8, CD4, CD25 or CD16.

2. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRp, respectively) or a variable γ and δ chains (also known as TCRy and TCR5, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or "antigen-binding fragment" of a TCR, which can be used interchangeably, refers to a molecule that contains a portion of the structural domains of a TCR, but that binds the antigen (e.g., MHC-peptide complex) to which the full TCR binds. In some cases, an antigen-binding portion contains the variable domains of a TCR, such as variable α chain and variable β chain of a TCR sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Chothia et al., 1988). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, $5^{th}$ ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the C-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell). T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

3. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

IV. Methods of Treatment

Further provided herein are methods for treating or delaying progression of cancer in an individual comprising administering to the individual an effective amount an antigen-specific T cell therapy, such as a VGLL1-specific T cell therapy. Adoptive T cell therapies with genetically engineered TCR-transduced T cells (conjugate TCR to other bioreactive proteins (e.g., anti-CD3) are also provided herein. In further embodiments, methods are provided for the treatment of cancer comprising immunizing a subject with a purified tumor antigen or an immunodominant tumor antigen-specific peptide.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. Additional exemplary cancers include, but are not limited to, lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer. Further examples cancers include melanomas, malignant melanomas, colon carcinomas, lymphomas, sarcomas, blastomas, renal carcinomas, gastrointestinal tumors, gliomas, prostate tumors, bladder cancer, rectal tumors, stomach cancer, oesophageal cancer, pancreatic cancer, liver cancer, mammary carcinomas, uterine cancer, cervical cancer, acute myeloid leukaemia (AML), acute lymphoid leukaemia (ALL), chronic myeloid leukaemia (CML), chronic lymphocytic leukaemia (CLL), leukaemia, hepatomas, various virus-induced tumors such as, for example, papilloma virus-induced carcinomas (e.g. cervical carcinoma), adenocarcino-mas, herpes virus-induced tumors (e.g. Burkitt's lymphoma. EBV-induced B cell lymphoma), hepatitis B-induced tumors (hepatocell carcinomas), HTLV-1- and HTLV-2-induced lymphomas, acoustic neuroma, lung carcinomas, small-cell lung carcinomas, pharyngeal cancer, anal carcinoma, glioblastoma, rectal carcinoma, astrocytoma, brain tumors, retinoblastoma, basalioma, brain metastases, medulloblastomas, vaginal cancer, pancreatic cancer, testicular cancer, Hodgkin's syndrome, meningiomas, Schneeberger disease, hypophysis tumor, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumors, oligodendroglioma, vulval cancer, intestinal cancer, colon carcinoma, oesophageal carcinoma, wart involvement, tumors of the small intestine, craniopharyngeomas, ovarian carcinoma, genital tumors, ovarian cancer, pancreatic carcinoma, endometrial carcinoma, liver metastases, penile cancer, tongue cancer, gall bladder cancer, leukaemia, plasmocytoma, lid tumor, and prostate cancer.

In some embodiments, T cells are autologous. However the cells can be allogeneic. In some embodiments, the T cells are isolated from the patient themself, so that the cells are autologous. If the T cells are allogeneic, the T cells can be pooled from several donors. The cells are administered to the subject of interest in an amount sufficient to control, reduce, or eliminate symptoms and signs of the disease being treated.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m² fludarabine is administered for five days.

In certain embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

The T cell may be administered intravenously, intramuscularly, subcutaneously, topically, orally, transdermally, intraperitoneally, intraorbitally, by implantation, by inhalation, intrathecally, intraventricularly, or intranasally. The appropriate dosage of the T cell therapy may be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

A. Pharmaceutical Compositions

Also provided herein are pharmaceutical compositions and formulations comprising antigen-specific T cell therapy and a pharmaceutically acceptable carrier. A vaccine composition for pharmaceutical use in a subject may comprise a tumor antigen peptide (e.g., VGLL1) composition disclosed herein and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22$^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Combination Therapies

In certain embodiments, the compositions and methods of the present embodiments involve an antigen peptide or antigen-specific T cell population in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

A T cell therapy may be administered before, during, after, or in various combinations relative to an additional cancer therapy, such as immune checkpoint therapy. The administrations may be in intervals ranging from concurrently to minutes to days to weeks. In embodiments where the T cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an antigen peptide or antigen-specific T cell therapy is "A" and an anti-cancer therapy is "B":

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzclesin and bizelesin synthetic analogues); cryptophycins (particularly cryptophycin 1 and cryptophycin 8); dolastatin; duocarmycin (including the synthetic analogues, KW-2189 and CB1-TMI); cleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as ncocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin, anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above, 2. Radiotherapy Other factors that cause DNA damage and have been used extensively include what are commonly known as T-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA®. (trastuzumab emtansine or T-DMI) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998, Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

V. Articles of Manufacture or Kits

An article of manufacture or a kit is provided comprising antigen-specific T cells or antigen peptides (e.g., VGLL1 peptide) is also provided herein. The article of manufacture or kit can further comprise a package insert comprising instructions for using the antigen-specific T cells to treat or delay progression of cancer in an individual or to enhance immune function of an individual having cancer. Any of the antigen-specific T cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification and Characterization of Tumor Antigen-Specific Peptides A pancreatic patient-derived tumor organoid cell line (hMIA-2d) was obtained (Cold Spring Harbor Laboratories) to identify HLA-restricted peptides in pancreatic tumors. HLA class I was immunoprecipitated and peptides were acid-eluted and analyzed by tandem mass spectrometry. About 1800 peptides were detected from the tumor cell line and, of these, 10 peptides were potentially targetable (i.e., demonstrated low or absent expression in essential normal tissues). The top eluted peptide from the pancreatic cancer patient MP015 was VGLL1 (Table 1) which is predicted to bind to multiple HLA class I allotypes (Table 2). The same peptide was also detected in a second HLA-A*0101-positive pancreatic organoid tumor cell line derived from a different patient MP081 (Table 1). The VGLL1 peptide identity was verified by targeted mass spectrometric detection comparing the mass spectra of the natural peptides with an isotope-labeled (i.e., heavy lysine, $C^{15}+N^{13}$) peptide (FIGS. 1A-1D).

TABLE 1

VGLL1-derived peptide was detected by MS in PDAC tumor organoid samples from 2 HLA-A*0101-positive patients.

| Patient tumor sample identifier | Eluted peptide | Gene Symbol | Gene Description | Ion Score | Match Rank | Tumor RNAseq (TPM) | m/z [Da] | Delta Mass [PPM] |
|---|---|---|---|---|---|---|---|---|
| MP015 | LSELETPGKY | VGLL1 | Vestigial-like 1 | 28 | 1 | 77.53 | 568.797 | 2.69 |
| MP081 | LSELETPGKY | VGLL1 | Vestigial-like 1 | 48 | 1 | 56.39 | 568.795 | 0.11 |

| Patient tumor sample identifier | Matched Ions | Total Ions | Predicted HLA binding affinity (nM) | | | | | |
|---|---|---|---|---|---|---|---|---|
| | | | A01:01 | A26:01 | B38:01 | C04:01 | C12:03 | B35:02 |
| MP015 | 8 | 80 | 51 | 12558 | 29369 | 30164 | 6181 | 33903 |
| | | | A01:01 | A01:01 | B57:01 | C04:01 | C06:02 | B35:02 |
| MP081 | 9 | 80 | 51 | 51 | 11936 | 30164 | 35852 | 33903 |

TABLE 2

VGLL1-derived peptide is predicted to bind multiple HLA class I allotypes.

| Gene | Peptide | HLA allotype | Predicted binding affinity (nM) | World HLA prevalence (%) | Highest regional HLA prevalence (%) |
|---|---|---|---|---|---|
| VGLL1 | LSELETPGKY | HLA-A*0101 | 51 | 9.5 | England, Ireland (37) Germany, Austria (34) USA (28) France (26) Israel (23) |
| VGLL1 | LSELETPGKY | HLA-A*2902 | 1117 | 3.2 | S. and Central Africa (18) Switzerland (10) Chile (10) USA (9) Portugal (8) |
| VGLL1 | LSELETPGKY | HLA-A*3002 | 166 | 3.0 | S. and Central Africa (21) Israel (16) Cuba (10) Portugal (9) Brazil (7) |

Figure 2A:
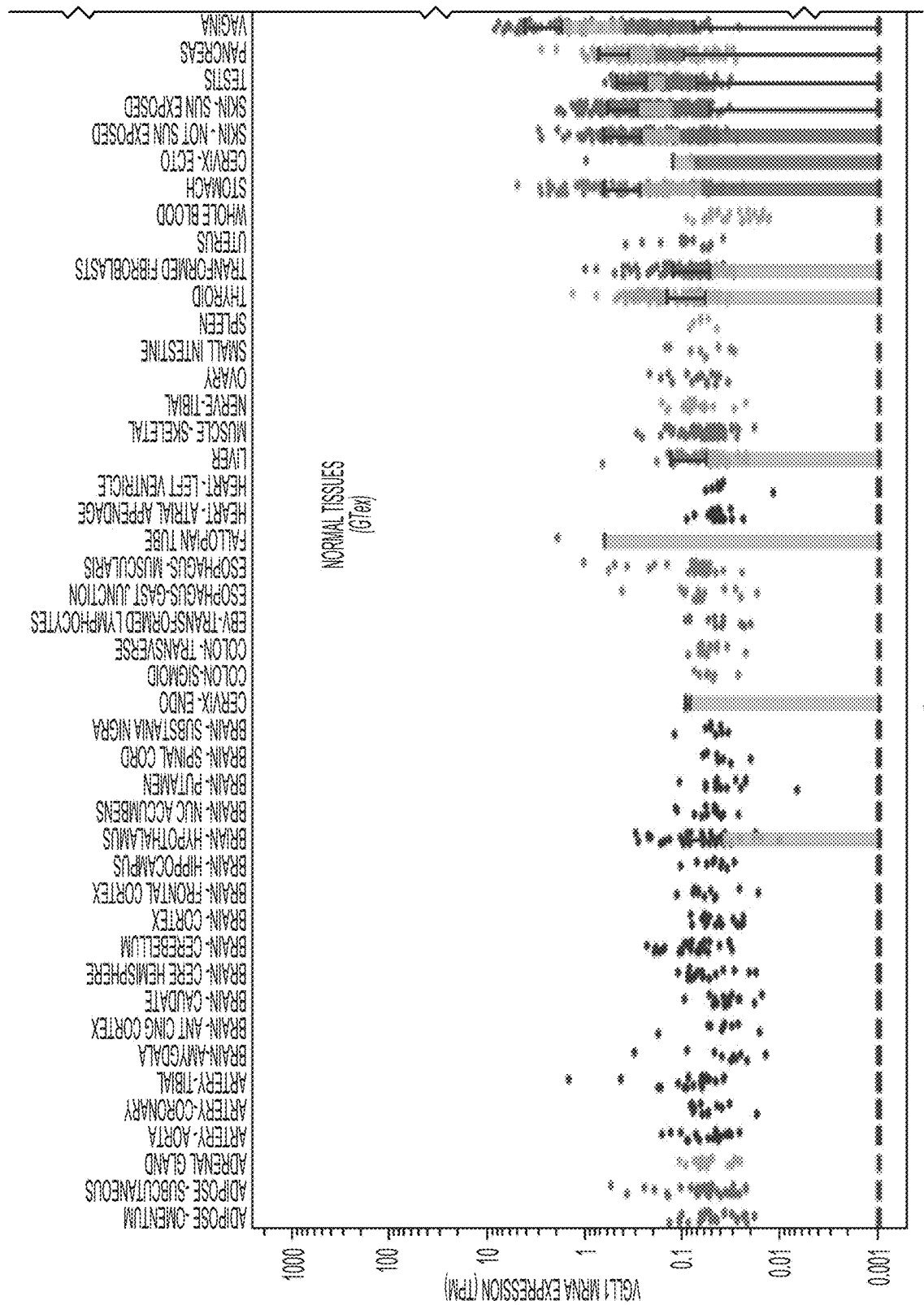
FIGS. 2A-2B: VGLL1 mRNA transcripts are overexpressed in several tumor types compared with normal tissues. (A) RNAseq analysis derived from the GTex Portal normal tissue (gtexportal.org) and TCGA (cancergenome.nih.gov) tumor tissue databases show VGLL1 transcript expression in normal tissues and various cancers, respectively. Each dot represents the results of one analyzed human sample. The left star and arrow indicates the highest mean normal tissue level of VGLL1 transcript, found in bladder. The right star and arrow indicates the level of VGLL1 transcript in the MP015 patient-derived organoid cell line hMIA2D, from which the VGLL1 peptide was detected. Boxes indicate the 5 cancer types that overexpress VGLL1 transcripts: pancreatic, ovarian, bladder, breast, and stomach cancers. TPM, transcripts per million. (B) VGLL1 expression prevalence in five cancer types derived from TCGA data. Tumor-associated expression was considered positive if VGLL1 mRNA expression was >3 TPM, as determined by RNAseq expression.
Figure 2A:
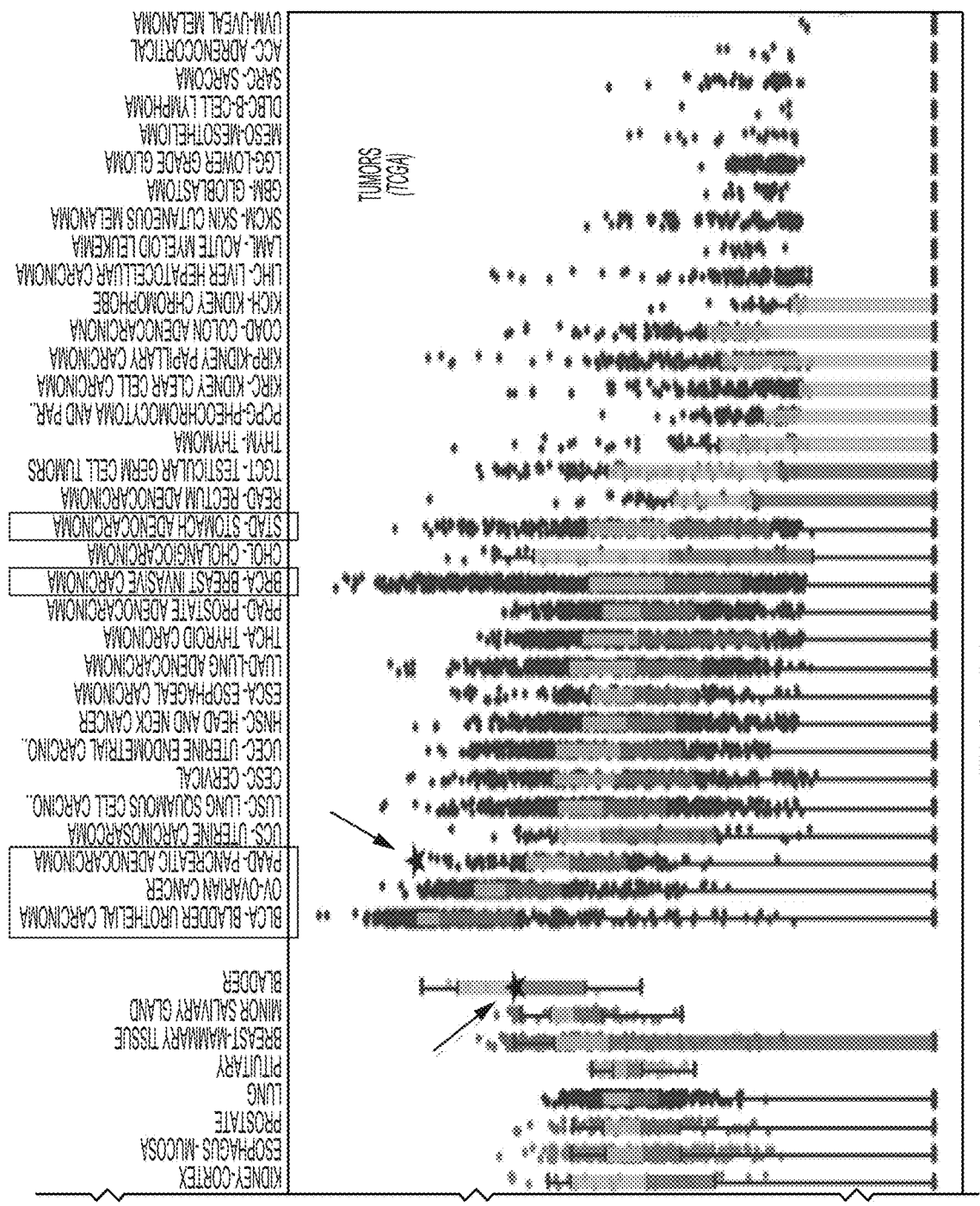
Figure 2B:
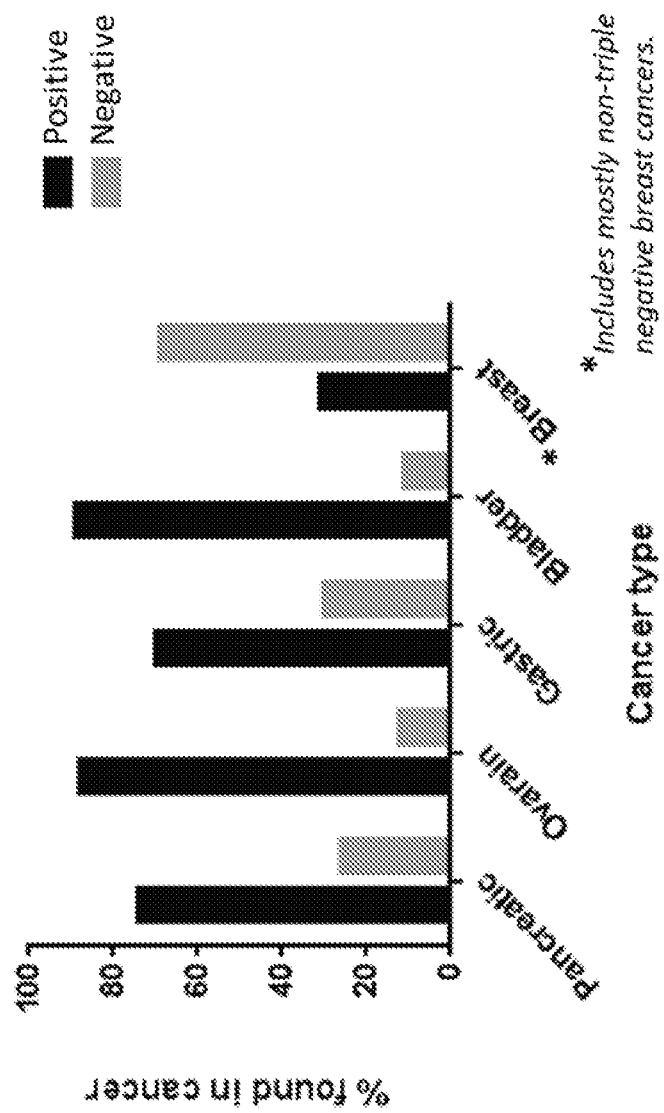

The expression of the VGLL1 gene was evaluated in normal tissue and tumor cell lines using RNA sequencing (FIG. 2A). According the Cancer Genome Atlas, the vast majority of normal tissues have effectively no expression of VGLL1, while tumor cells, particularly pancreatic, bladder, ovarian, uterine, breast, and cervical cancer, have elevated expression of VGLL1. The prevalence of VGLL1 overexpression in these TGCA cancers is summarized in FIG. 2B. Thus, VGLL1 is a tumor-associated, co-transcriptional activator with limited expression in normal tissues.

Figure 4A:
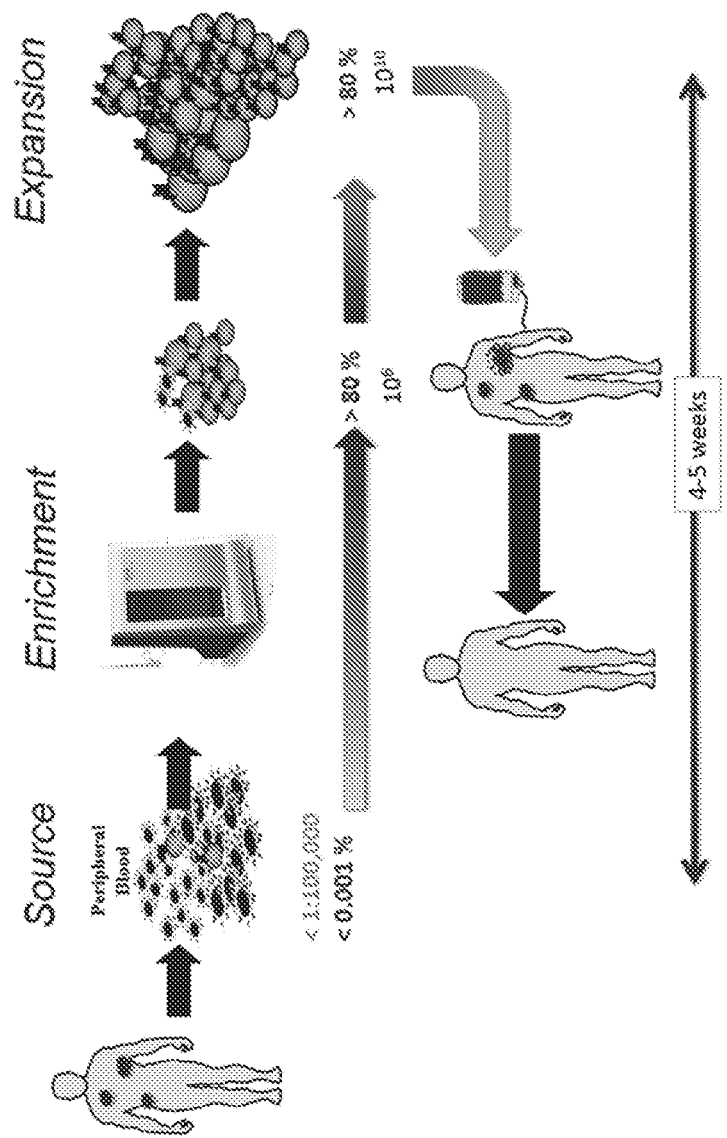
FIGS. 4A-4D: VGLL1 peptide-specific cytotoxic T cells were isolated and expanded from PDAC patient peripheral blood and infused for treatment. (A) Schematic depicting adoptive T cell treatment process. (B) Peripheral blood from HLA-A*0101-positive PDAC patient MP015 were stimulated twice with autologous LSELETPGKY (SEQ ID NO: 1) peptide-pulsed dendritic cells, prior to 2 rounds of tetramer-based OWL sorting and rapid expansion protocol (REP). (C) VGLL1-specific CTLs were expanded to ~20 billion cells and infused into patient MP015 with concurrent anti-PD1 treatment every three weeks. (D) The CTL infusion induced no serious toxicities nor any apparent clinical benefits, despite showing robust autologous antitumor activity in vitro. Gene expression analysis performed on multiple longitudinal tumor samples from patient MP015 revealed that VGLL1 antigen loss occurred during the intervening months between harvest of the original tumor (source of the organoid cell line hMIA-2D) and VGLL1-specific CTL infusion.
Figure 4B:
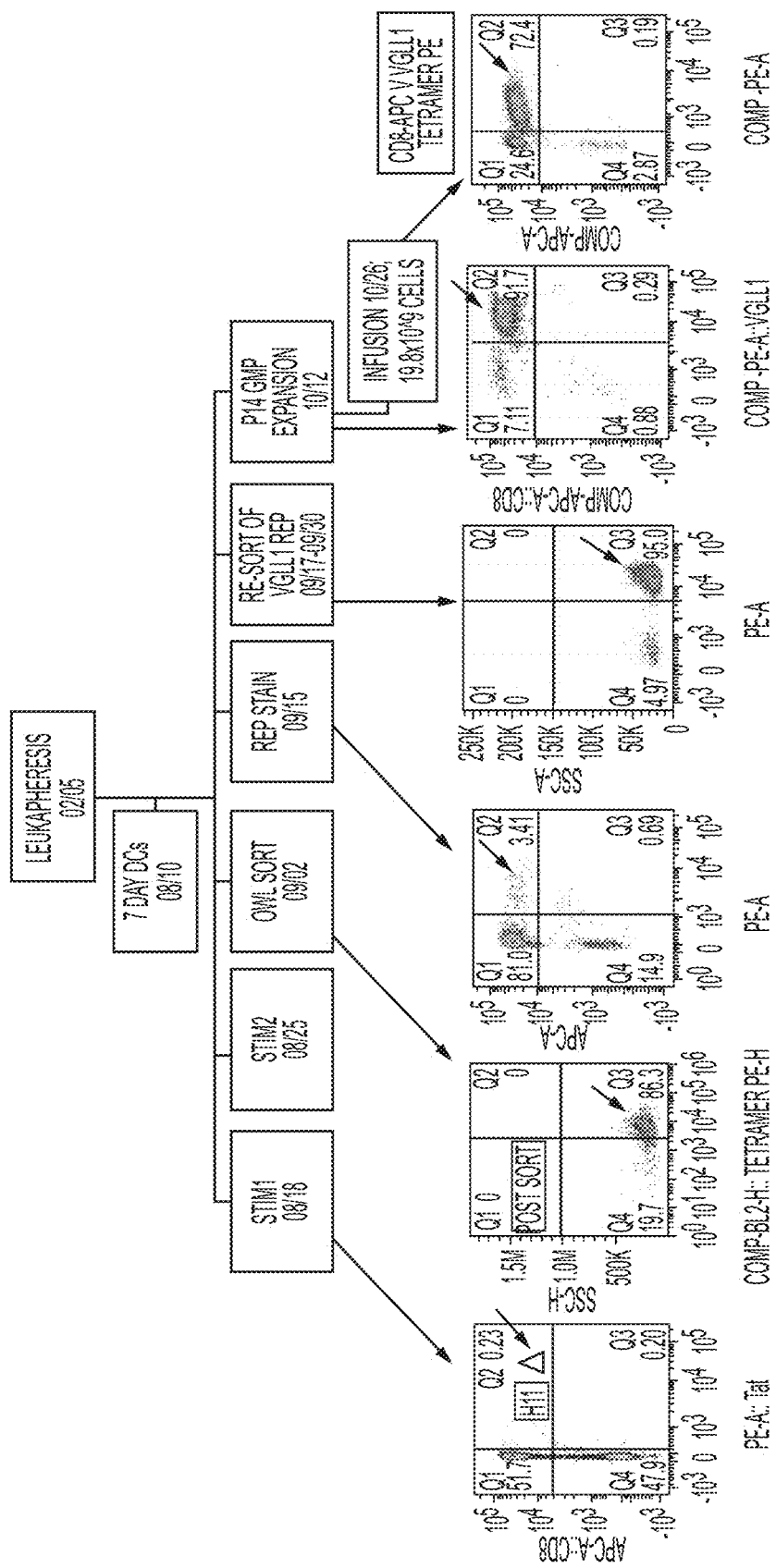

Clinical grade peptide and peptide-HLA-A*0101 tetramers were synthesized and used to generate VGLL1-specific CTL (FIG. 4A). VGLL1-specific CD8$^+$ T cells were generating by stimulating autologous patient PBMCs with VGLL1 peptide-pulsed dendritic cell treated with IL-21. CD8 T cells were sorted using tetramer-based sorting and expanded by the Rapid Expansion Protocol (REP) to generate ~$10^7$ million T cells of which 91.7% were CD8 and tetramer positive (FIG. 4B).

Figure 5A:
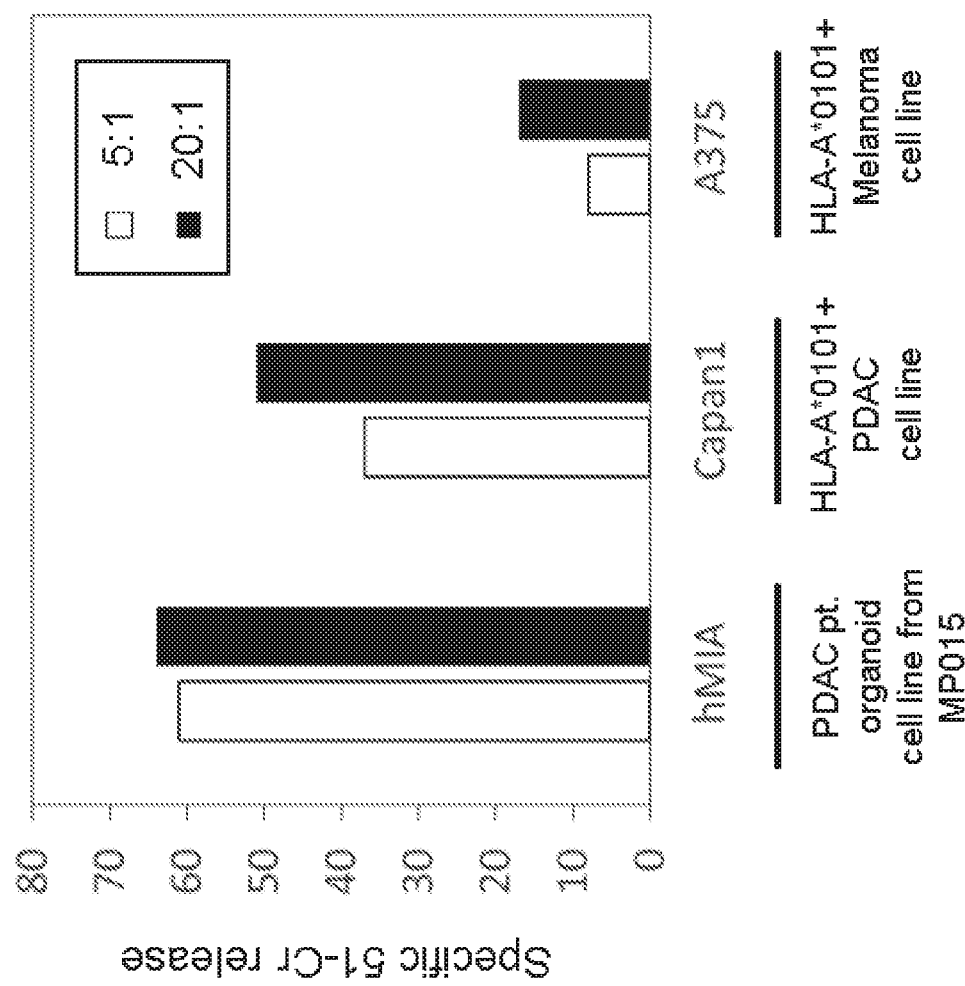
FIGS. 5A-5B: VGLL1-specific CTLs recognize and kill patient-derived and allogeneic HLA-A*0101+ pancreatic cancer cells. (A) Expanded HLA-A*0101-restricted VGLL1-specific CD8+ T cells were co-cultured with autologous PDAC patient MP015-derived tumor line hMIA-2D, HLA-A*0101-positive PDAC cell line Capan-1, or HLA-A*0101-positive melanoma cell line A375 in a standard 51Cr release assay to measure cytotoxic activity at effector-to-target (E:T) cell ratios of 5:1 and 20:1. (B) Same cytotoxicity assay as in (A), except all three cell lines were pulsed with 1 mM cognate VGLL1 peptide antigen and washed prior to VGLL1-specific CTL exposure.
Figure 5B:
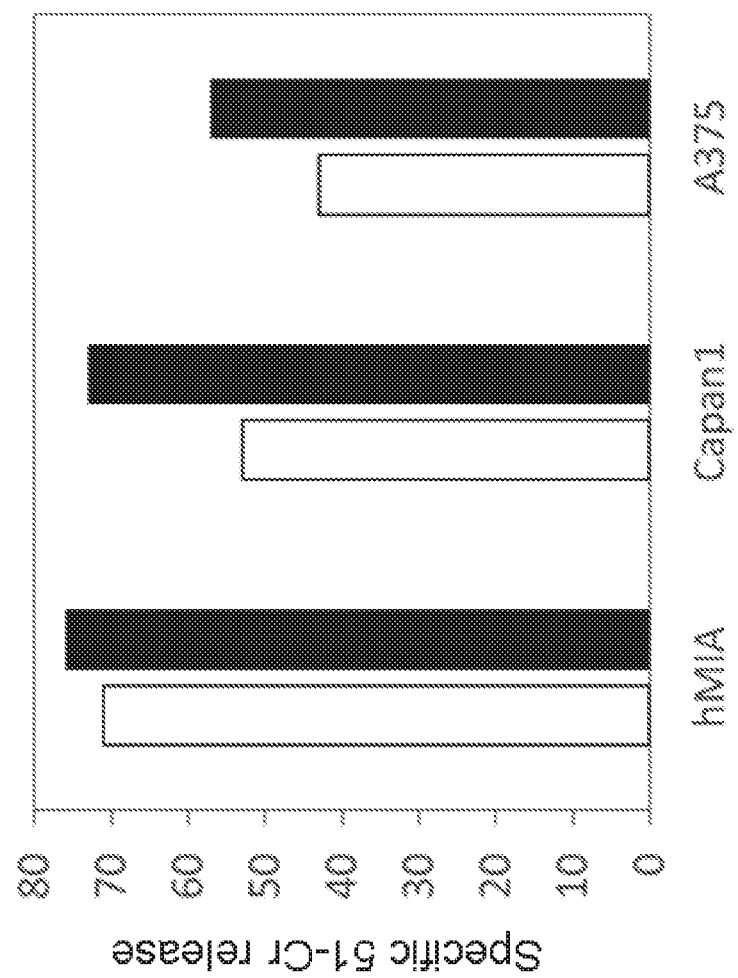

To determine the ability of VGLL1-specific CD8$^+$ T cells to recognize and kill VGLL1-expressing cells, a standard $^{51}$Cr release assay was performed using HLA-A*0101-positive pancreatic tumor cell lines. The VGLL1-expanded T cells showed about 70% killing of patient tumor cell line hMIA-2D and slightly lower killing of one other HLA-A1 pancreatic cell line Capan-1 by $^{51}$Cr release assay (FIG. 5). This showed that VGLL1-specific CD8$^+$ T cells could recognize the VGLL1 epitope endogenously processed by pancreatic cells. As controls, HLA-A*0101 positive melanoma cells negative for VGLL1 expression (A375) were used.

Figure 6A:
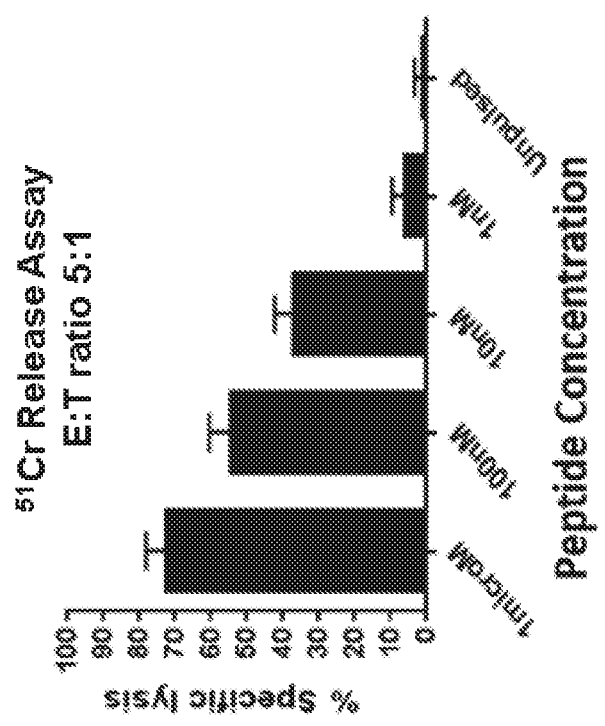
FIGS. 6A-6C: VGLL1-specific CTLs kill HLA-A0101+ tumor cell lines derived from pancreatic, bladder, ovarian, and triple-negative breast cancers. (A) Expanded HLA-A*0101-restricted VGLL1-specific CD8+ T cells were co-cultured with HLA-A*0101-positive Mel888 melanoma cells pulsed with titrated amounts of cognate VGLL1 peptide in a standard 51Cr release cytotoxicity assay at a 5:1 effector-to-target (E:T) cell ratio. (B) Cytotoxicity assay results of VGLL1-specific CTLs tested against six HLA-A*0101-positive cell lines, including four PDAC lines (hMIA-2D, Capan-1, BXPC3, and MP081), a triple-negative breast cancer line (BT20), and a bladder cancer line (UBLC1) at a 5:1 E:T cell ratio. (C) Cytotoxicity assay results of VGLL1-specific CTLs tested against two additional HLA-A*0101-positive cell lines, a triple-negative breast cancer line (BT549) and an ovarian cancer line (OAW28), with or without prior interferon-gamma treatment at a 5:1 E:T cell ratio.
Figure 6B:
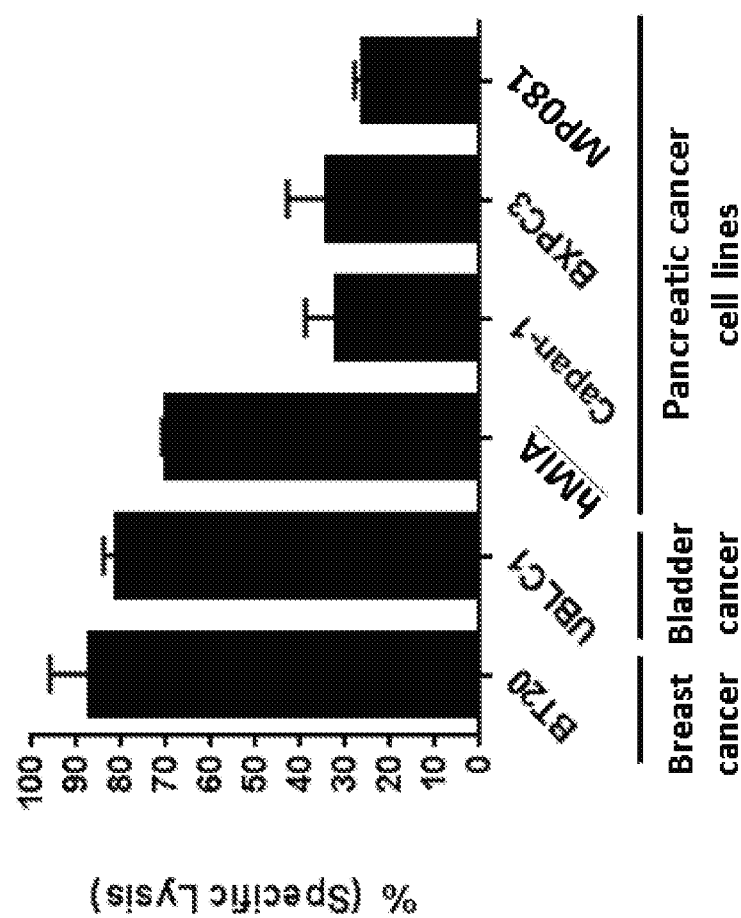
Figure 6C:
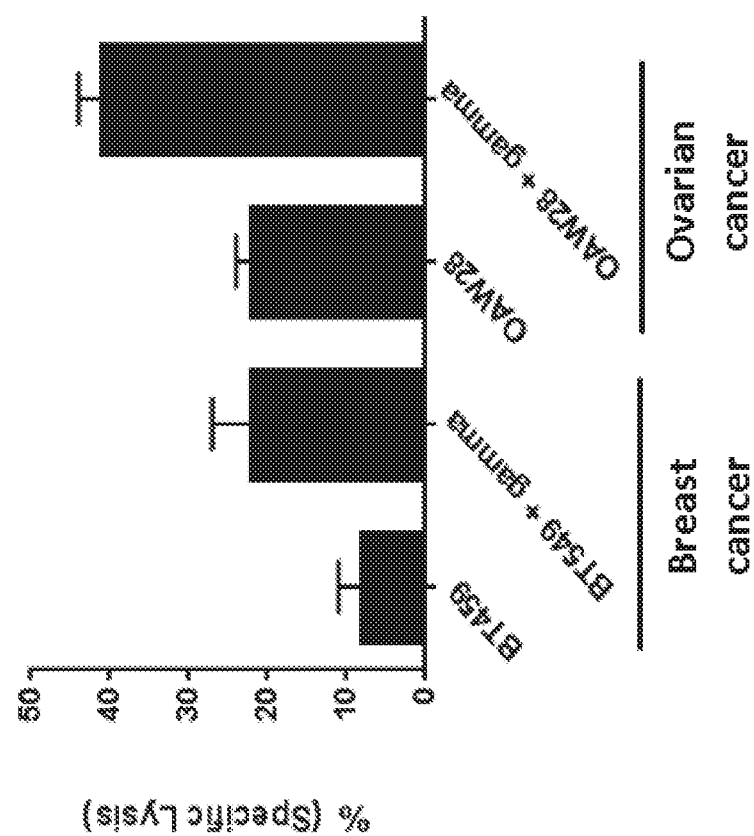
Figure 7A:
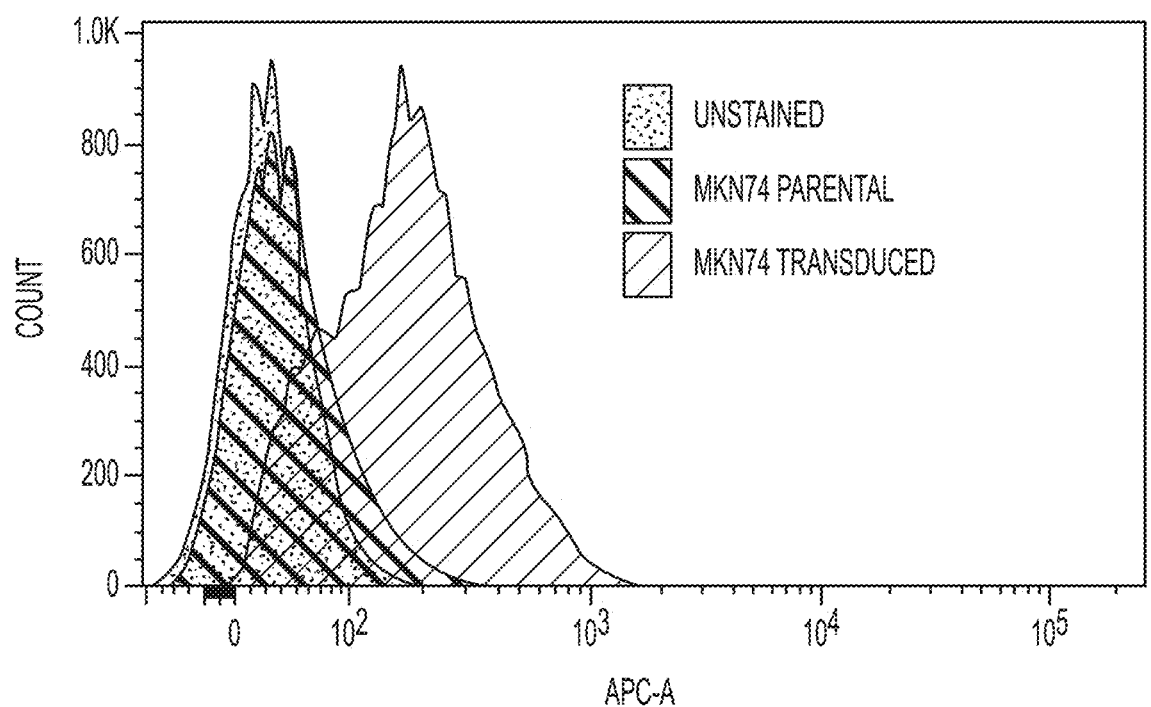
FIGS. 7A-7B: Gastric cancer line MKN74 is killed by VGLL1-specific CTLs following HLA-A*0101 transduction. (A) Flow cytometric analysis of parental MKN74 gastric cancer cells and MKN74 cells transduced with a lentiviral vector to express HLA-A*0101. Cells were stained with a HLA-A*0101-specific mAb and analyzed by flow cytometry. The MKN74 transduced cells are shifted to the right. (B) Cytotoxicity assay results of VGLL1-specific CTLs tested against untransduced HLA-A*0101-positive melanocytes or the same melanocytes lentivirally transduced to express VGLL1 at a 5:1 E:T cell ratio.
Figure 7B:
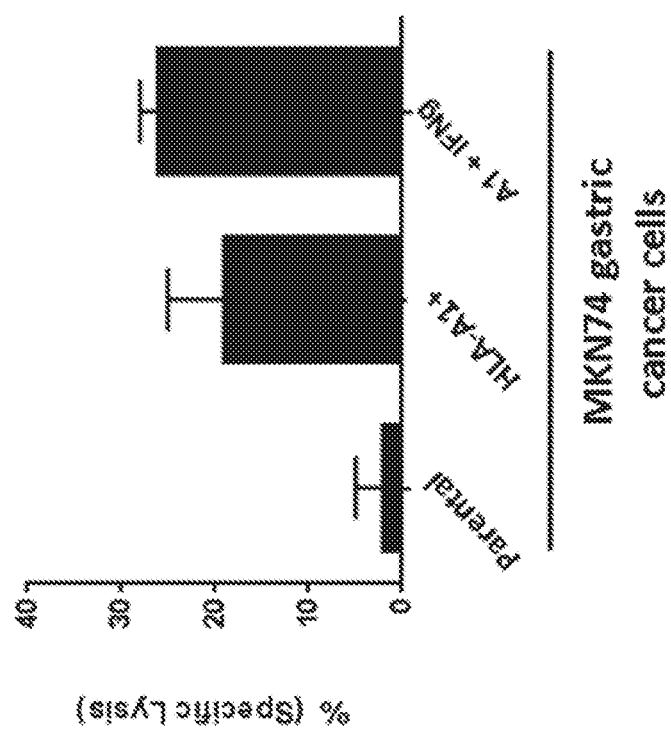

In addition, other cancer cell types were cultured with VGLL1-specific CTLs and the cytotoxicity was measured by chromium release assay. It was observed that the VGLL1-specific CTLs were capable of recognizing and killing multiple HLA-A*0101-positive tumor cell types including breast, ovarian, and bladder tumor cell lines (FIG. 6). An HLA-A*0101-negative gastric cell line was not recognized by VGLL1-specific T cells, but upon transduction to express HLA-A*0101 the cell line was recognized and killed. This showed that gastric cancer cells also expresses VGLL1, and CTL-specific killing could be further enhanced by prior treatment with interferon-gamma (FIG. 7).

Figure 4C:
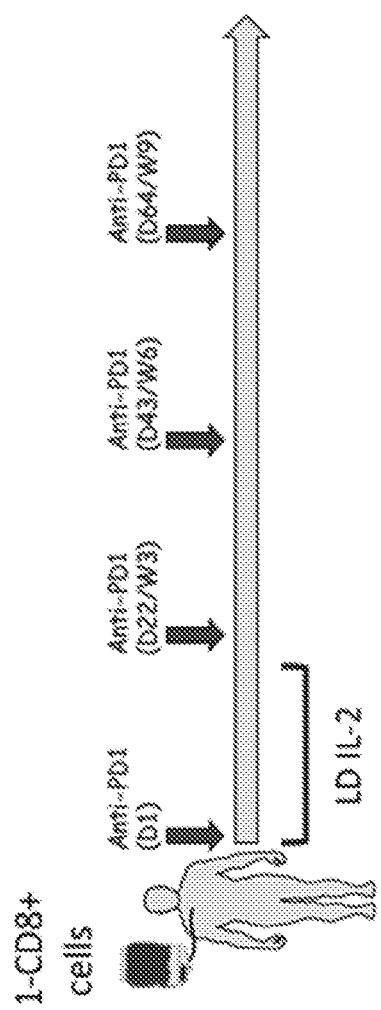
Figure 4D:
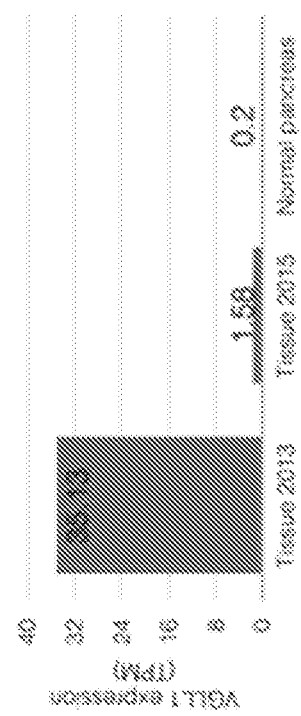

Following further T-cell expansion (FIG. 4B), the pancreatic cancer patient MP015 was infused with 19.8 billion expanded VGLL1-specific T cells in conjunction with anti-PD1 antibody pembrolizumab every three weeks and low dose subcutaneous IL-2 (250,000 U/m$^2$ every 12 h) (FIG. 4C). No clinical response was observed due to VGLL1 antigen loss (FIG. 4D) and the patient experienced little or no treatment-related toxicity. Importantly, no cell-infusion-associated adverse events were observed.

T cell receptor analysis of the sorted T cell product which was more than 95% tetramer positive for the target antigen, revealed that 99% of the TCR sequences were restricted to 21 clonotypes, with the dominant clone representing 43% of all sequences. HTTCS tracking of peripheral blood samples revealed a cumulative frequency (representing all 21 clonotypes) of 1.7% of total T cells in the PBMC with the dominant clonotype comprising more than 1% of total T cells. One month later, the transferred antigen-specific T cells were present at very low but detectable levels (0.03%) in the periphery, however they had accumulated in the pleural effusion biopsy (0.37%). No infiltration into the lung tumor tissue was detected.

Overall, these results suggest that a relevant tumor-associated antigenic epitope can be identified from patient tumor sample, and was of sufficient immunogenicity to elicit autologous pancreatic tumor-reactive, antigen-specific T cells from patient peripheral blood. Isolation and expansion of such T cells for adoptive transfer was feasible and the transferred T cells achieved relatively high frequency in the peripheral blood with apparent enrichment in the pleural effusion where they were detected at high frequency more than a month later. Thus, the antigen-specific peptides identified, such as VGLL1, can be used to generate antigen-specific T cells for adoptive T cells transfer in the treatment of solid cancers, such as pancreatic and other cancer types.

Figure 3:
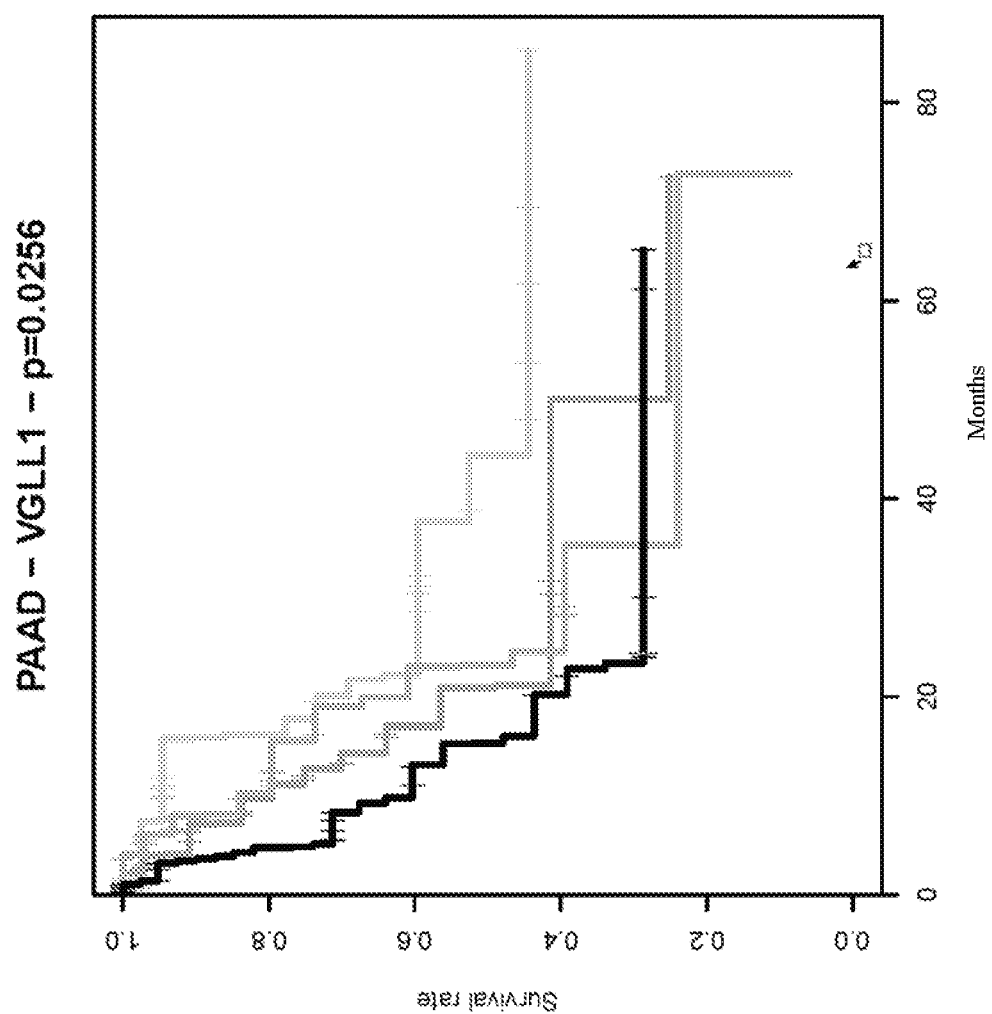
FIG. 3: Elevated VGLL1 expression is a poor prognostic factor in cancer. Pancreatic patient survival analysis, as divided into quartiles of highest (black line), $2^{nd}$ highest (dark gray), 3rd highest (medium gray), and lowest (light gray) VGLL1 tumor transcript expression, as determined by TCGA RNAseq data. The lowest VGLL1 expression correlated with highest survival rate.

Further, an analysis was performed using The Cancer Genome Atlas database to correlate survival rates of pancreatic cancer patients based on VGLL1 transcript expression (FIG. 3) as well as other cancers. It was observed that overall survival rate significantly correlated with VGLL1 expression as the patients with the highest VGLL1 expression (top quartile) had the worst overall survival rate. Conversely, patients with the lowest VGLL1 expression (bottom quartile) showed the longest overall survival. Thus, VGLL1 is a tumor marker that may be used as a prognostic marker in cancer patients, specifically pancreatic cancer patients.

Example 2—Materials and Methods

Cell Lines:

hMIA-2d cell were maintained in RPMI1640 with 4 mM L-glutamine, 1 mM non-essential amino acids, 10 mM sodium pyruvate and 50 U/ml penicillin, 50 mg/ml streptomycin and 10% FBS (TCB). LCL used as feeder cells and cultured with RPMI 1640 containing 10% FBS, 50 U/ml penicillin, 50 mg/ml and streptomycin. CTL media for T cell culture contained 10% FBS, 2 mM L-glutamine, β-mercaptoethanol, 50 U/ml penicillin and 50 mg/ml streptomycin.

MP015 patient-derived tumor cells (hMIA-2d) were expanded to approximately 10E8 cells (10×10 cm confluent plates), then lysed using Triton X-100. Cell lysates were incubated overnight at 4° C. with gentle agitation with 1 µg HLA-A,B,C specific mAb W6/32 for every 10 mg protein. Protein A/G Ultralink resin beads were used to immunoprecipitate HLA molecules, which were then directly eluted along with tumor-associated peptides using 0.1N acetic acid in five consecutive 1 mL eluates. Purification of HLA was confirmed by Western Blot analysis and HLA-positive elutes were pooled and analyzed by tandem mass spectrometry (MS/MS).

Mass Spectrometry:

For discovery phase tandem mass spectrometry (MS/MS), eluted MHC class I-bound peptides were injected onto a high-sensitivity HPLC system (Dionex 3000 RSLC), separated by reversed-phase chromatography in 0.1% formic acid water-acetonitrile on 1.8 micron C18 (Agilent Technologies) and analyzed on an Orbitrap Elite mass spectrometer (Thermo Scientific) using data-dependent acquisition. The Mascot algorithm searched acquired MS/MS spectra against the SwissProt complete human protein database using 10 ppm parent mass tolerance, 0.8 d fragment ion tolerance, Met oxidation, no enzyme selectivity. Search results were cross-referenced with the appropriate MHC-binding specificities using NetMHC 3.4. Approximately 1800 peptides were detected in Discovery phase MS/MS, all corresponding to wild-type sequences matching proteins within the human proteome.

Based on the results of Discovery MS/MS, whole exome sequencing, and bioinformatics analysis considering target gene expression in normal tissues (GTex RNAseq databases), human pancreatic tumors (TCGA RNAseq database), and the patient's own RNAseq analysis, 11 isotope-labeled high-confidence peptides of interest (8 mutated and 3 non-mutated) were synthesized and used as standards in a more sensitive targeted MS/MS analysis. In this analysis, retention-time windows for the synthetic peptide standards of interest were pre-determined by MS analysis of the synthetic peptides, then targeted methods for searching tumor-associated peptides were constructed using mass windows of 3 Da around each m/z. The targeted MS/MS experiments verified the presence of all 3 non-mutated peptides, but convincing MS evidence was not found for any of the predicted mutated peptides.

Generation and Expansion of VGLL1-Specific CD8 T Cells:

Tumor antigen-specific CTLs were generated with a manner previously described (Li, 2005). Leukapheresis PBMCs positive for HLA-A*0101 were stimulated by autologous DC pulsed with tumor antigen peptide. For induction of dendritic cells, adherent PBMCs were cultured with GM-CSF and IL-4 in AIM-V medium (Invitrogen Life Technologies) for 6 days and then added IL1b, IL-6, TNF-α and PGE2 for maturation. After 1 day, mature DCs were pulsed with 40 µg/ml peptide at $2 \times 10^6$ cells/ml of 1% human serum albumin (HAS)/PBS in the present of 3 µg/ml beta-microglobulin for 4 hr at room temperature. After washing with 1% HSA/PBS, DCs were mixed with PBMCs at $1.5 \times 10^6$ cell/ml/well in 48 well plate. IL-21 (30 ng/ml) was added initially and 3-4 days after culture. IL-2 and IL-7 were added 1 day after secondary stimulation to expand activated antigen-specific T cells.

6 days after secondary stimulation, cells were stained with VGLL1 peptide/MHC-PE-conjugated tetramer and CD8-APC antibody, and then CD8 and tetramer-positive cells were sorted by OWL sorting. The sorted VGLL1-specific CD8 T cells were expanded by Rapid Expansion Protocol (REP) with feeder cells of PBL and LCL under IL-21.

Peptide-MHC Tetramer Staining:

VGLL1-specific CD8 T cells were confirmed by staining with tetramer of VGLL1 peptide/HLA A*0101. CD8 T cells were incubated with PE-conjugated tetramer for 20 mins, washed and then stained with APC-conjugated CD8 antibody for 15 mins in room temperature. After washing, cells were analyzed by flow cytometry (LSRFortessa X-20 Analyzer).

$^{51}$Chromium Release Assay:

VGLL1-specific CD8 T cells were assayed for specific lysis of VGLL1-expressing or not expressing targets using standard $_{51}$Chromium ($_{51}$Cr) release assay. Targets were labeled with 100 uCi of $_{51}$Cr for 2 hrs and after three times washing, the labeled targets plated triplicated well at a 2000 targets per well. Effector cells were incubated with targets as various effector:target (E:T) ratio. After 4 hours, 30 ul of supernatant was collected from each well and the siCr was measured by a gamma counter. The percentage of specific lysis was calculated.

RNAseq Analysis:

Whole Transcriptome Seq (RNA-Seq) was performed by the Avera Institute for Human Genetics on tumor samples using the Illumina TruSeq Stranded Total RNA kit with Ribo-Zero Gold. Approximately 200 million Paired-End reads were used for each tumor RNA sample. BCL (raw output of Illumina HigSeq) files was processed using ISIS v2.4.60 for demultiplexing and conversion to FASTQ format. FASTQ files and sequence reads were aligned to the genome (Hg19) using BWA using parameters suitable for a specific run (for example, 3 mis-matches with 2 in the first 40 seed regions for a 51 bases sequencing run). The aligned BAM files were then subjected to mark duplication, re-alignment, and re-calibration using Picard and GATK programs before any downstream analyses. RNASeq data was processed using TopHat, TopHat-Fusion, and Cufflinks algorithms.

Statistical Analysis:

Data analysis was performed using GraphPad prism version 6.0e. Normally distributed data were analyzed using parametric tests (Anova or unpaired t-test). Statistical test differences were considered significant if p values were <0.05.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit scope and concept of the invention as defined by the appended claims.

REFERENCES

The following references, to the extent that they provide exemplary procedural or other details supplementary to those set forth herein, are specifically incorporated herein by reference.

Austin-Ward and Villaseca, *Revista Medica de Chile*, 126 (7):838-845, 1998.
Ausubel et al., *Current Protocols in Molecular Biology*, Greene Publishing Associates and John
Baird et al., *Scand. J. Immunol.*, 60(4):363-71, 2004.
Baraldo et al., *Infect. Immun.*, 73(9):5835-41, 2005.
Bijker et al., *J. Immunol.*, 179:5033-5040, 2007.
Biology Publications, p. 433, 1997.
Blanchard and Shastri, *Curr. Opin. Immunol.*, 20:82-88, 2008.
Bukowski et al., *Clinical Cancer Res.*, 4(10):2337-2347, 1998.
Burrows et al., *Trends Immunol.*, 27:11-16, 2006.
Camacho et al. (2004) *J Clin Oncology* 22(145): Abstract No. 2505, 2004.
Celluzzi et al., *J. Exp. Med.*, 183 283-287, 1996.
Chothia et al., *EMBO J.* 7:3745, 1988.
Christodoulides et al., Microbiology, 144(Pt 11):3027-3037, 1998.
Cohen et al. *J Immunol.* 175:5799-5808, 2005.
Cold Spring Harbor, N.Y. 2001.
Collins et al., *Nature*, 371:626-629, 1994.
Davidson et al., *J. Immunother.*, 21(5):389-398, 1998.
Davila et al. *PLoS ONE* 8(4): e61338, 2013.
Drin et al., *AAPSPharm. Sci.*, 4(4):E26, 2002.
Du et al., *J. Pept. Res.*, 51:235-243, 1998.
Dudley et al., *J. Immumol.*, 26(4):332-342, 2003.
Elliott and O'Hare, *Cell*, 88:23-233, 1997.
European Patent Application No. EP2537416

Fedorov et al., *Sci. Transl. Medicine*, 5(215), 2013.
Janeway et al, *Immunobiology: The Immune System in Health and Disease*, 3rd Ed., Current
Frankel and Pabo, Cell, 55:189-1193, 1988.
Goeddel, *Methods Enzymol.*, 185:3-7, 1990.
Guo et al., *Nature.* 360:364-366, 1992.
Gupta et al., *Biomaterials.* 26:3995-4021, 2005.
Hanibuchi et al., *Int. J. Cancer,* 78(4):480-485, 1998.
Heemskerk et al. *Hum Gene Ther.* 19:496-510, 2008.
Hellstrand et al., *Acta Oncologica.* 37(4):347-353, 1998.
Hollander, *Front. Immun.*, 3:3, 2012.
Hui and Hashimoto, *Injection Immun.*, 66(11):5329-5336, 1998.
Hurwitz et al., *Proc Natl Acad Sci USA* 95(17): 10067-10071, 1998.
International Patent Publication No. WO 00/37504
International Patent Publication No. WO 01/14424
International Patent Publication No. WO 98/42752
International Patent Publication No. WO/2014055668
International Patent Publication No. WO 1995001994
International Patent Publication No. WO1998042752
International Patent Publication No. WO2000037504
International Patent Publication No. WO200014257
International Patent Publication No. WO2001014424
International Patent Publication No. WO02006/121168
International Patent Publication No. WO2007/103009
International Patent Publication No. WO2009/101611
International Patent Publication No. WO2009/114335
International Patent Publication No. WO2010/027827
International Patent Publication No. WO2011/066342
International Patent Publication No. WO2012/129514
International Patent Publication No. WO02013/071154
International Patent Publication No. WO2013/123061
International Patent Publication No. WO2013/166321
International Patent Publication No. WO2013126726
International Patent Publication No. WO2014/055668
International Patent Publication No. WO2014031687
International Patent Publication No. WO2015016718
Johnson et al. Bkod 114:535-46, 2009.
Jores et al., *PNAS U.S.A.* 87:9138, 1990.
Lefranc et al., Dev. Comp. Immunol. 27:55, 2003.
Li, *Nat Biotechnol.* 23:349-354, 2005.
Lin et al., *J. Biol. Chem.*, 270:4255-14258, 1995.
Melief and van der Burg, *Nat. Rev. Cancer,* 8:351-360, 2008.
Mellman et al., *Nature* 480:480-489, 2011.
Mokyr et al. *Cancer Res* 58:5301-5304, 1998.
Moorthy et al., *PLoS Med.,* 1(2):e33, 2004.
Neelapu et al., *Blood.* 15:109(12):5160-5163, 2007.
Pardoll, *Nature Rev Cancer* 12:252-264, 2012.
Parkhurst et al. *Clin Cancer Res.* 15: 169-180, 2009.
Popescu et al. *Blood,* 15:109(12):5407-5410, 2007.
Qin et al., *Proc. Natl. Acad. Sci. USA,* 95(24):14411-14416, 1998.
Quintarelli et al., *Blood.* 117:3353-3362, 2011.
Rojas et al., *J. Biol. Chem.,* 271:27456-27461, 1996.
Rojas et al., *Proc. West. Pharmacol. Soc.,* 41:55-56, 1998.
Sadelain et al., *Cancer Discov.* 3(4): 388-398, 2013.
Sambrook et al., *Molecular Cloning: A Laboratory Manual,* 3rd ed., Cold Spring Harbor Press,
Samino et al., *J. Biol. Chem.,* 281:6358-6365, 2006.
Schwarze et al., *Trends in Cell Biol.,* 10:290-295, 2000.
Schwenzer et al., *J. Biol. Chem.,* 274:19368-19374, 1999.
Stryhn et al., *Eur. J. Immunol.,* 30:3089-3099, 2000.
Terakura et al. *Blood.* 1:72-82, 2012.
Turtle et al., *Curr. Opin. Imniumol.,* 24(5): 633-39, 2012.
U.S. Pat. No. 4,373,071
U.S. Pat. No. 4,401,796
U.S. Pat. No. 4,458,066
U.S. Pat. No. 4,598,049
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 6,225,042
U.S. Pat. No. 6,355,479
U.S. Pat. No. 6,362,001
U.S. Pat. No. 6,410,319
U.S. Pat. No. 6,451,995
U.S. Pat. No. 6,790,662
U.S. Pat. No. 7,070,995
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 8,008,449
U.S. Pat. No. 8,017,114
U.S. Pat. No. 8,119,129
U.S. Pat. No. 8,252,592
U.S. Pat. No. 8,324,353
U.S. Pat. No. 8,329,867
U.S. Pat. No. 8,339,645
U.S. Pat. No. 8,354,509
U.S. Pat. No. 8,398,282
U.S. Pat. No. 8,479,118
U.S. Pat. No. 8,735,553
U.S. Patent Publication No. 2002/131960
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. 2011/0008369
U.S. Patent Publication No. 2013/0149337
U.S. Patent Publication No. 2013/287748
U.S. Patent Publication No. 2014/022021
U.S. Patent Publication No. 2014/0294898
Varela-Rohena et al. *Nat Med.* 14: 1390-1395, 2008.
Wang and Wang, *Nat. Biotechnol.,* 20:149-154, 2002.
Wang et al. *J Immunother.* 35(9):689-701, 2012.
Wiley & Sons, N Y, 1994.
Wu et al., *Cancer,* 18(2): 160-75, 2012.
Yee et al. *Immunological reviews* 257: 250-263, 2014.
Yee et al., *J. Immunol. Methods,* 261(1-2): 1-20, 2002.
Young et al., *J. Exp. Med.,* 183:-11, 1996.
Zwaveling et al., *J. Immunol.,* 169:350-358, 2002.

What is claimed is:

1. A pharmaceutical composition comprising a vestigial-like 1 (VGLL1) peptide of 35 amino acids in length or less comprising an amino acid sequence having at least 90% sequence identity to SEQ ID NO: 1 and a pharmaceutical carrier, wherein the peptide is capable of inducing cytotoxic T lymphocytes (CTLs) and the pharmaceutical carrier is not only water.

2. The composition of claim 1, wherein the peptide comprises an amino acid sequence of SEQ ID NO: 1.

3. The composition of claim 1, wherein the peptide binds to a human class I HLA protein.

4. The composition of claim 3, wherein the human class I HLA protein is from the HLA-A1 family, the HLA-A29 family, the HLA-A30 family, the HLA-B18 family, or the HLA-B44 family.

5. The composition of claim 3, wherein the human class I HLA protein is HLA-A*0101, HLA-A*0102, HLA-A*0103, HLA-A*2902, HLA-A*3002, HLA-B*1801, or HLA-B*4403.

6. The composition of claim 1, wherein the peptide is 30 amino acids in length or less.

7. A method of promoting an immune response in a subject, comprising administering an effective amount of a vestigial-like 1 (VGLL1) peptide of 35 amino acids in length or less comprising an amino acid sequence having at least 90% sequence identity to SEQ ID NO: 1, wherein the peptide induces VGLL1-specific T cells in the subject.

8. The method of claim 7, wherein the subject is diagnosed with cancer.

9. The method of claim 8, wherein the cancer is pancreatic, ovarian, gastric, or breast cancer.

10. The method of claim 7, further comprising administering at least a second anti-cancer therapy.

11. The method of claim 10, wherein the second anti-cancer therapy is selected from the group consisting of a chemotherapy, a radiotherapy, an immunotherapy, or a surgery.

12. The method of claim 11, wherein the immunotherapy is an immune checkpoint inhibitor.

13. The method of claim 12, wherein the immune checkpoint inhibitor is an anti-PD1 monoclonal antibody.

14. The composition of claim 1, wherein the peptide is comprised in a liposome, lipid-containing nanoparticle, or in a lipid-based carrier.

15. The composition of claim 1, wherein the pharmaceutical composition is formulated for injection or inhalation as a nasal spray.

16. The composition of claim 1, wherein the pharmaceutical carrier is a non-aqueous solvent, oil, dispersion media, coating, surfactant, antioxidant, preservative, isotonic agent, absorption delaying agent, salt, drug, drug stabilizer, gel, binder, excipient, disintegration agent, and/or lubricant.

17. The composition of claim 1, wherein the pharmaceutical composition further comprises an adjuvant.

* * * * *

UNITED STATES PATENT AND TRADEMARK OFFICE
CERTIFICATE OF CORRECTION

| | |
|---|---|
| PATENT NO. | : 11,684,657 B2 |
| APPLICATION NO. | : 16/339981 |
| DATED | : June 27, 2023 |
| INVENTOR(S) | : Lizée et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1093 days.

Signed and Sealed this
Twelfth Day of November, 2024

Katherine Kelly Vidal
*Director of the United States Patent and Trademark Office*